United States Patent [19]

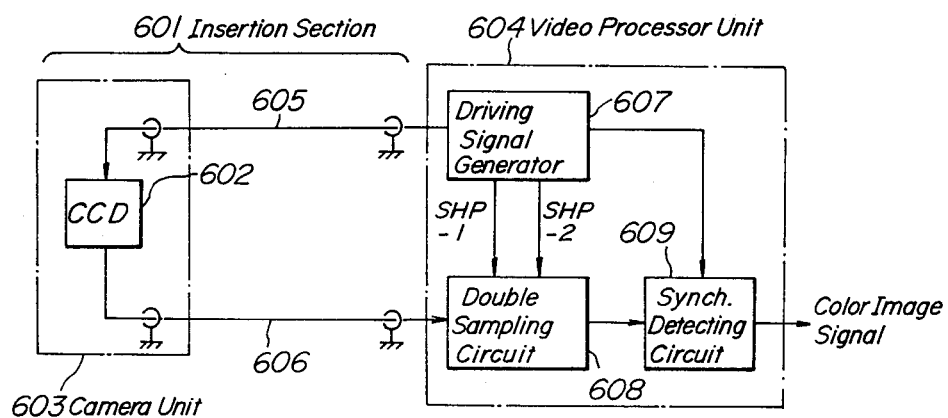
FIG_1
PRIOR ART

Kimura et al.

[11] Patent Number: 4,860,095
[45] Date of Patent: Aug. 22, 1989

[54] VIDEO CAMERA APPARATUS AND VIDEO ENDOSCOPE APPARATUS WITH MEANS FOR COMPENSATING IMAGE ERRORS CAUSED BY DIFFERING CABLE LENGTHS

[75] Inventors: Kenji Kimura, Tachikawa; Kiyoshi Tsuji, Tanashi, both of Japan

[73] Assignee: Olympus Optical Co., Ltd., Tokyo, Japan

[21] Appl. No.: 179,625

[22] Filed: Apr. 8, 1988

[30] Foreign Application Priority Data

| | | |
|---|---|---|
| Apr. 21, 1987 [JP] | Japan | 62-99458 |
| May 6, 1987 [JP] | Japan | 62-110062 |
| May 6, 1987 [JP] | Japan | 62-110063 |
| May 7, 1987 [JP] | Japan | 62-109666 |
| Aug. 17, 1987 [JP] | Japan | 62-203628 |
| Feb. 17, 1988 [JP] | Japan | 63-32811 |

[51] Int. Cl.$^4$ .......................... H04N 7/18; A61B 1/06
[52] U.S. Cl. ........................................ 358/98; 358/149
[58] Field of Search ............... 358/98, 222, 229, 160, 358/149

[56] References Cited

U.S. PATENT DOCUMENTS 4,667,230 5/1987 Arakawa et al. ................. 358/98
4,706,118 11/1987 Kato et al. ........................ 358/98

Primary Examiner—James J. Groody
Assistant Examiner—Victor R. Kostak
Attorney, Agent, or Firm—Stevens, Davis, Miller & Mosher

[57] ABSTRACT

A video endoscope apparatus including an insertion section insertable into a cavity of a patient body under inspection a solid state image sensor arranged at a distal end of the insertion section for converting an optical image of the cavity into an electric signal a video processor unit including a driving circuit for generating a driving signal including vertical and horizontal driving pulses and a reset pulse for the solid state image sensor, and a video processing circuit for processing the electric signal supplied from the solid state image sensor to derive an image signal to be displayed on a monitor is provided with circuitry for compensating for image signal distortion caused by aberrations in the driving and reset pulses received at the insertion section due to differing signal cable lengths between the insertion section and the video processing unit.

36 Claims, 37 Drawing Sheets

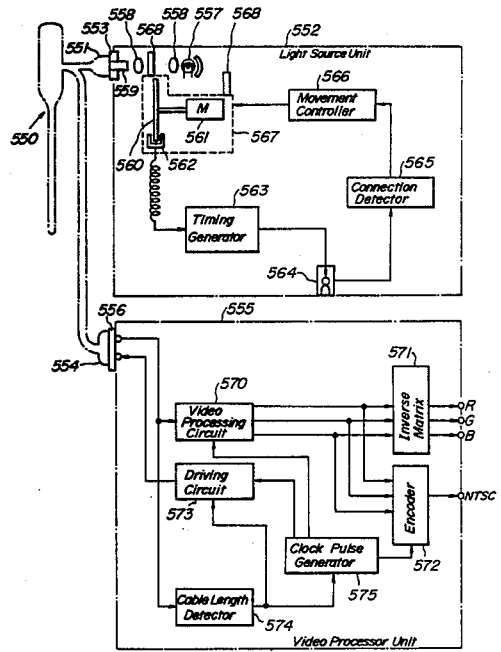

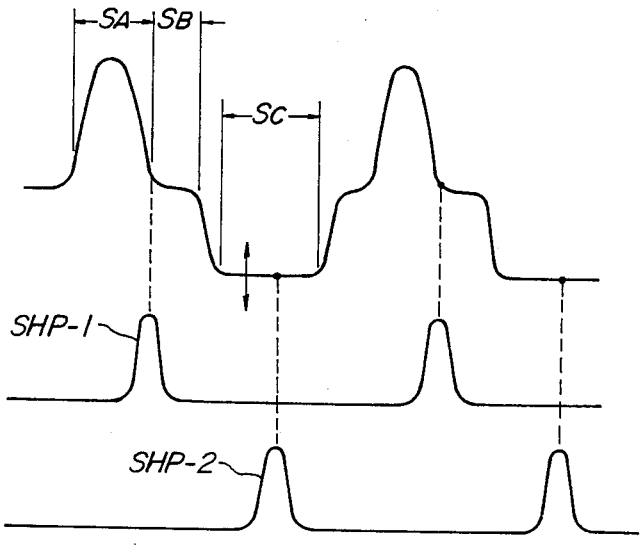
FIG_2A PRIOR ART
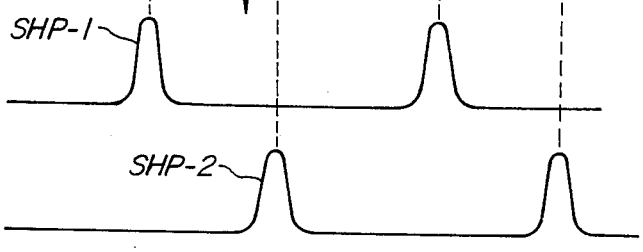
FIG_2B PRIOR ART
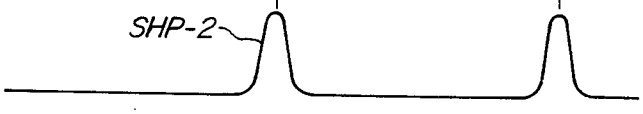
FIG_2C PRIOR ART

FIG_3
PRIOR ART
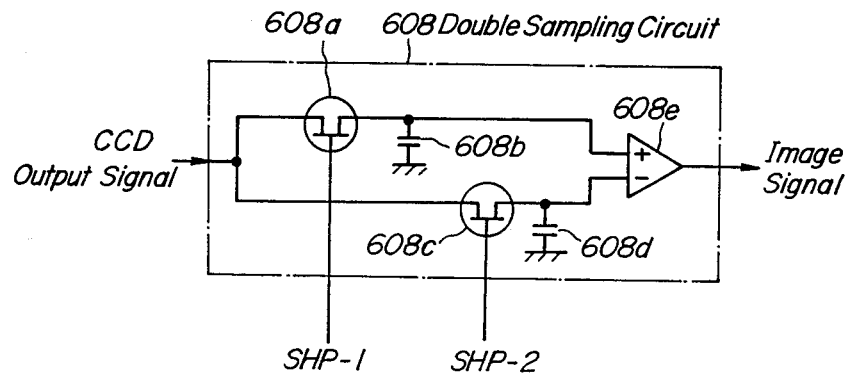
FIG_4A
PRIOR ART
FIG_4B
PRIOR ART
FIG_4C
PRIOR ART
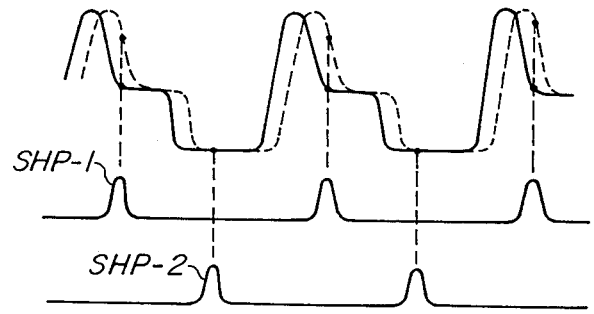

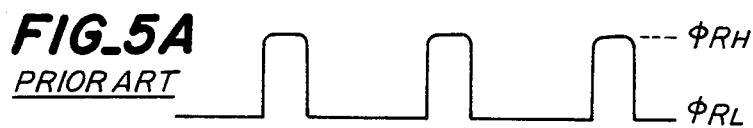
FIG_5A PRIOR ART
FIG_5B PRIOR ART
FIG_5C PRIOR ART
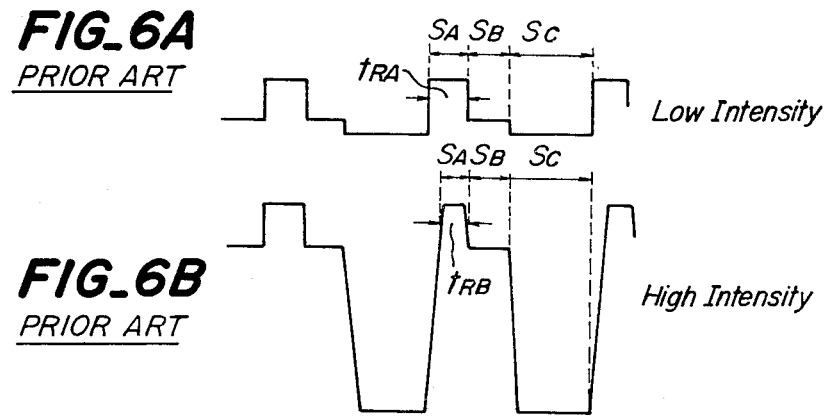
FIG_6A PRIOR ART
FIG_6B PRIOR ART

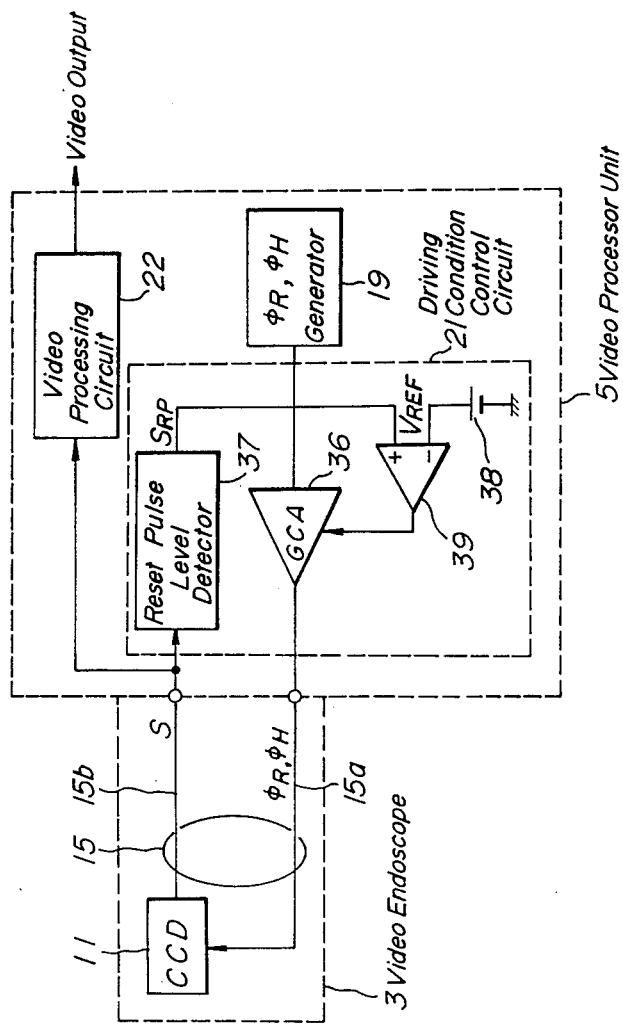

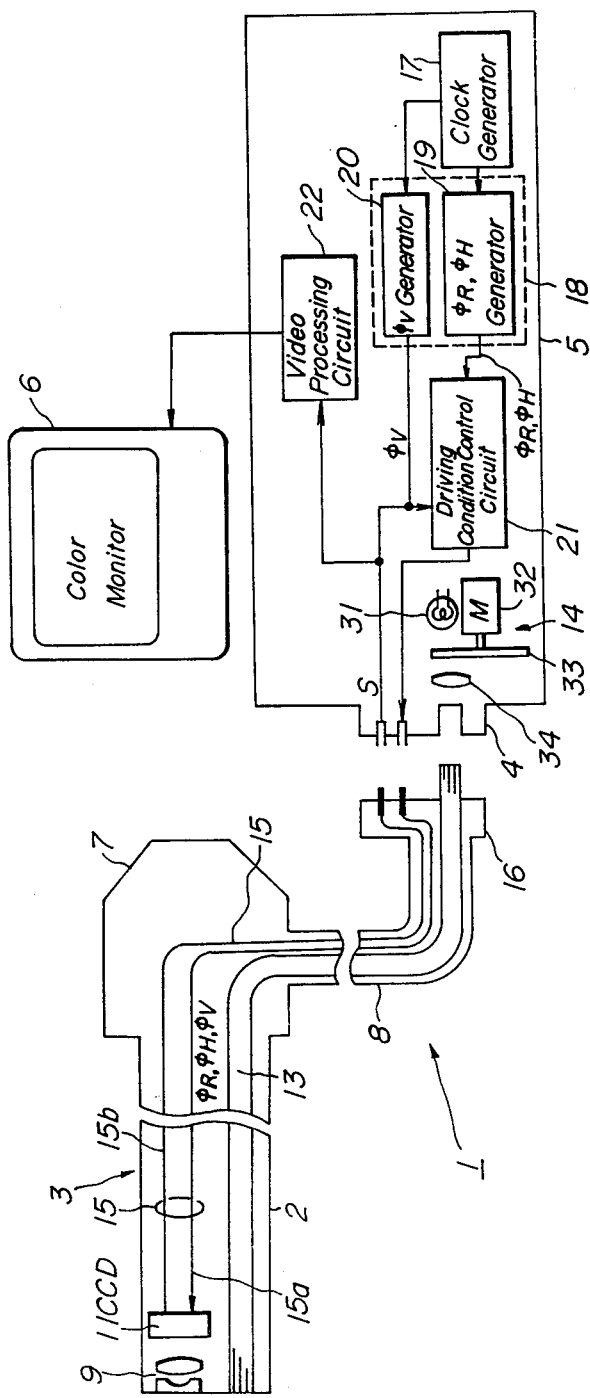

FIG_11

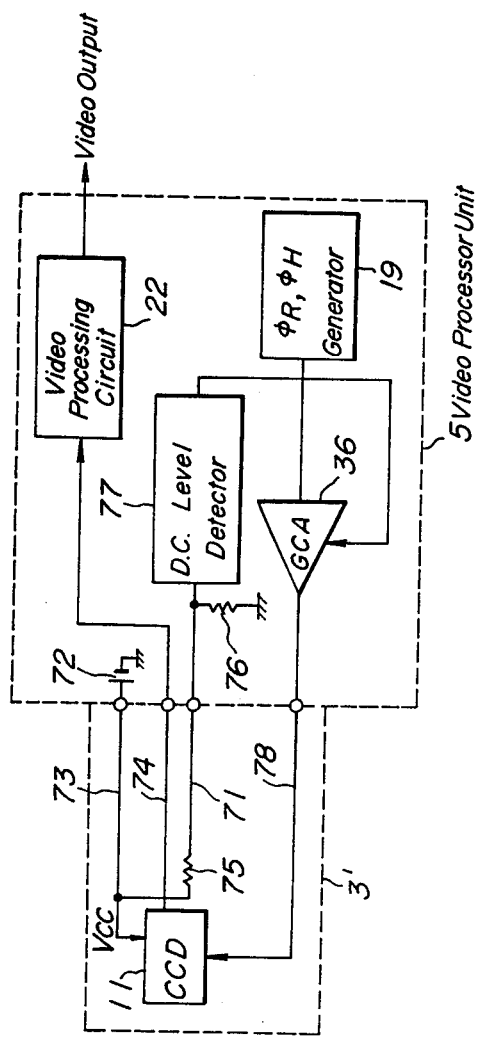
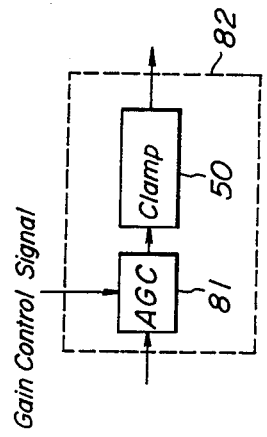
FIG.13
FIG.14

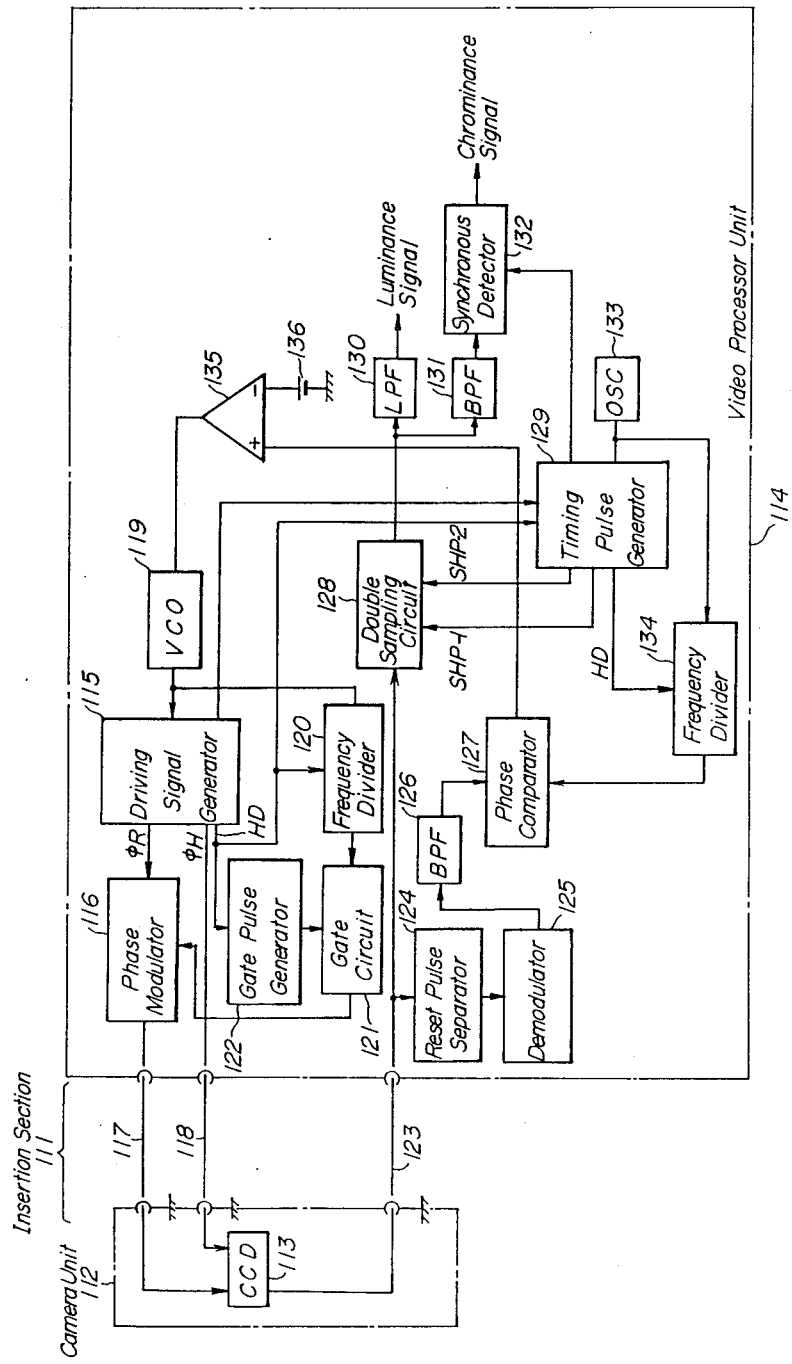
FIG_15

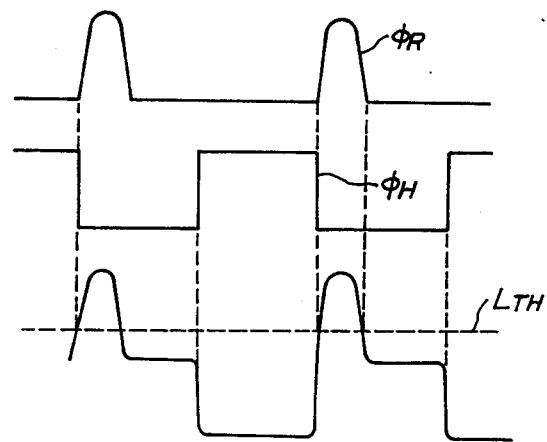

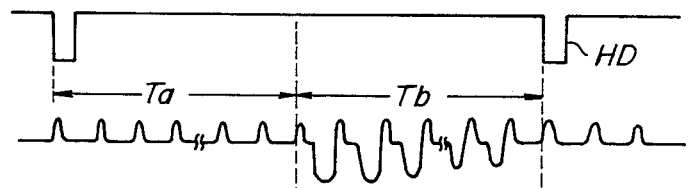
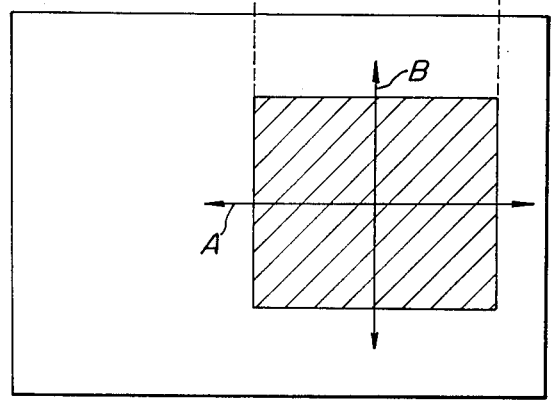

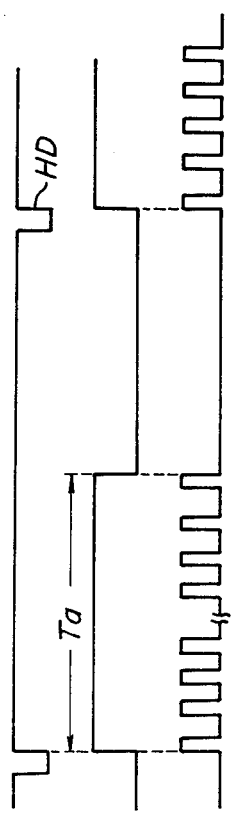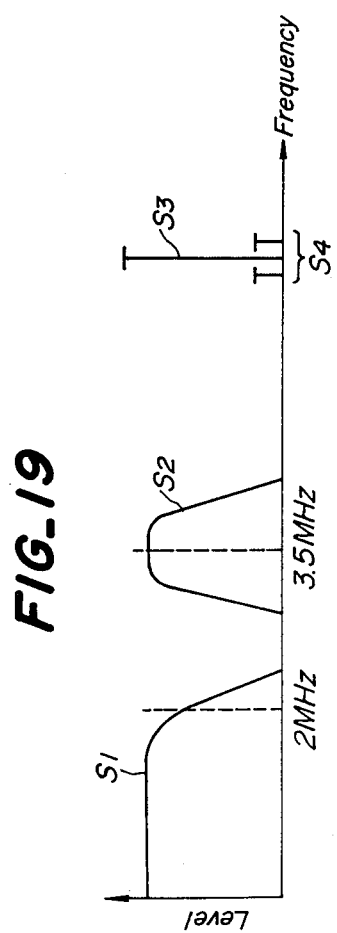

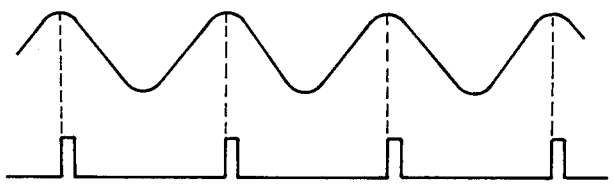
FIG.20A
FIG.20B
FIG.21
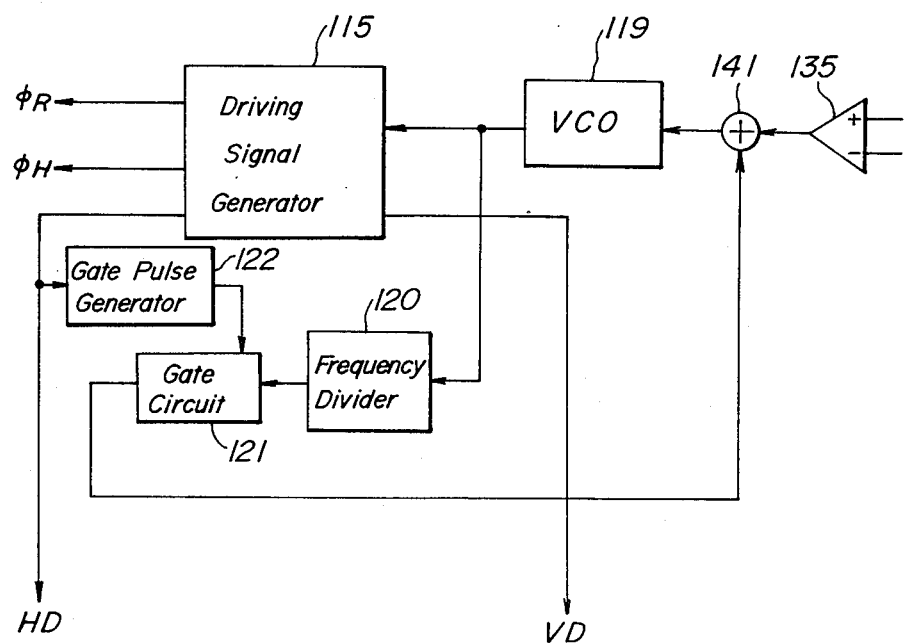

FIG_23A 
FIG_23B 

FIG_26A 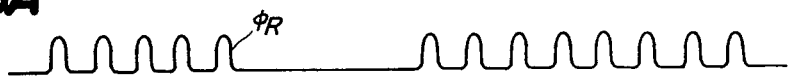
FIG_26B 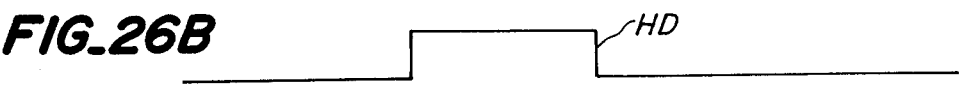

FIG_28
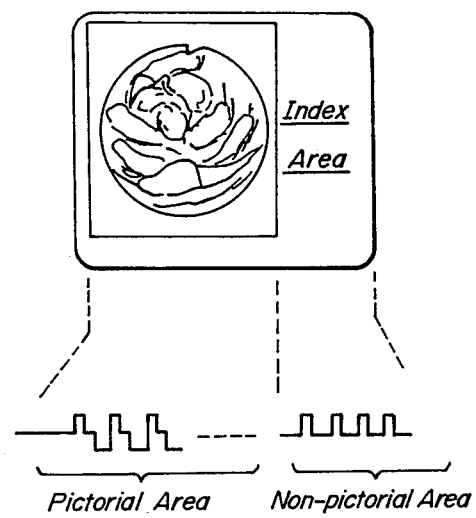
Pictorial Area    Non-pictorial Area
FIG_29
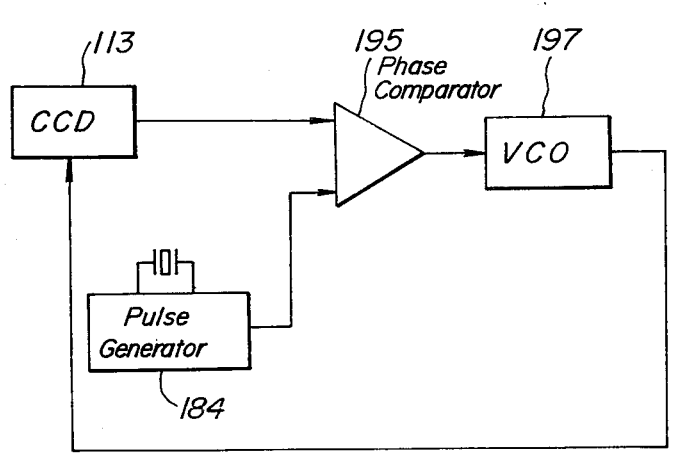

FIG_31

FIG_34
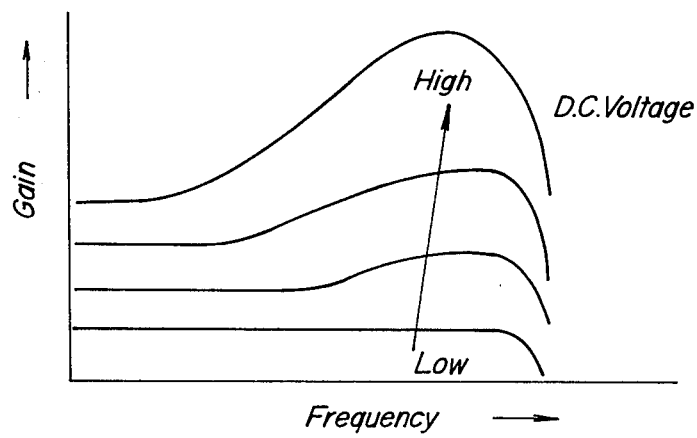
FIG_35
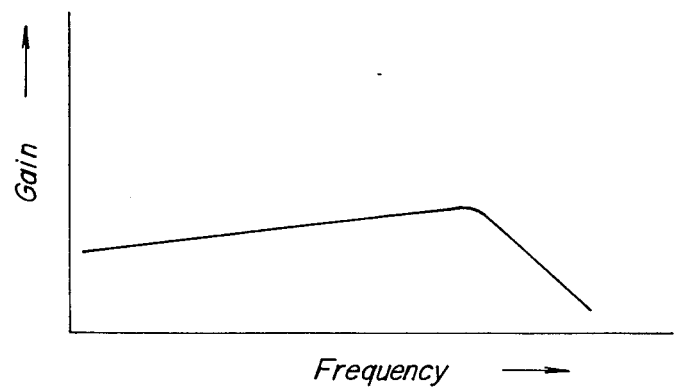

FIG_36
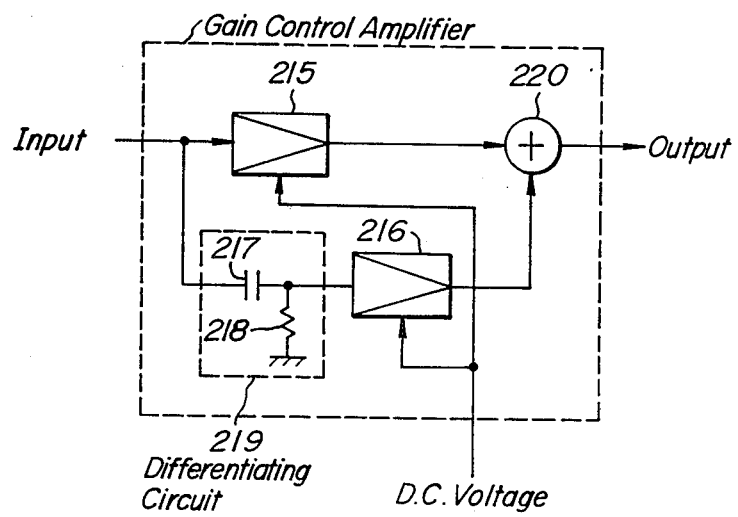

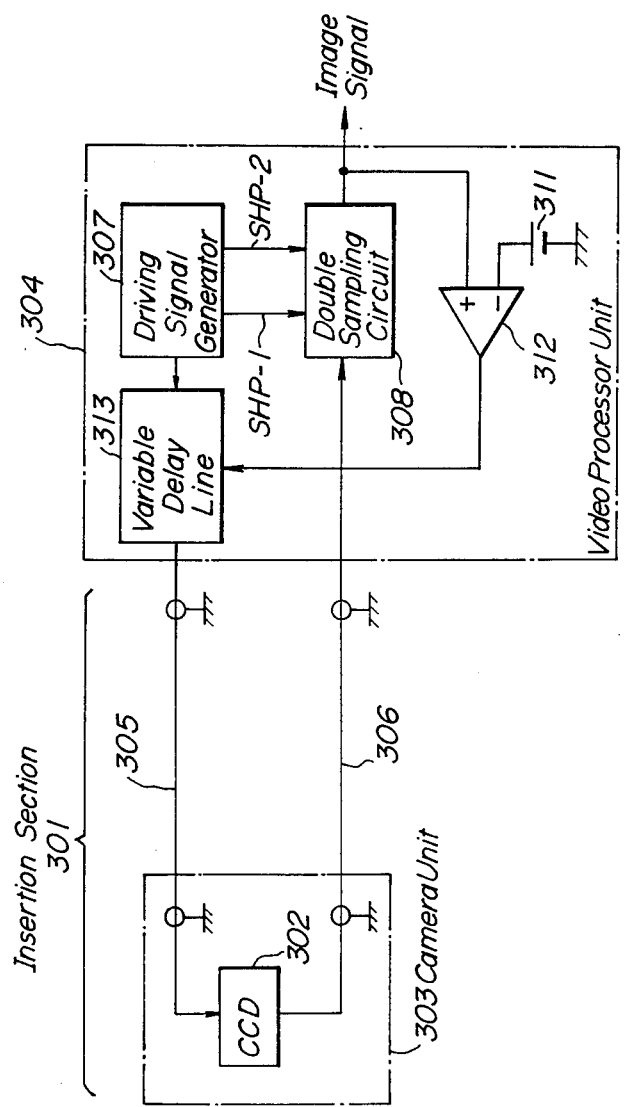

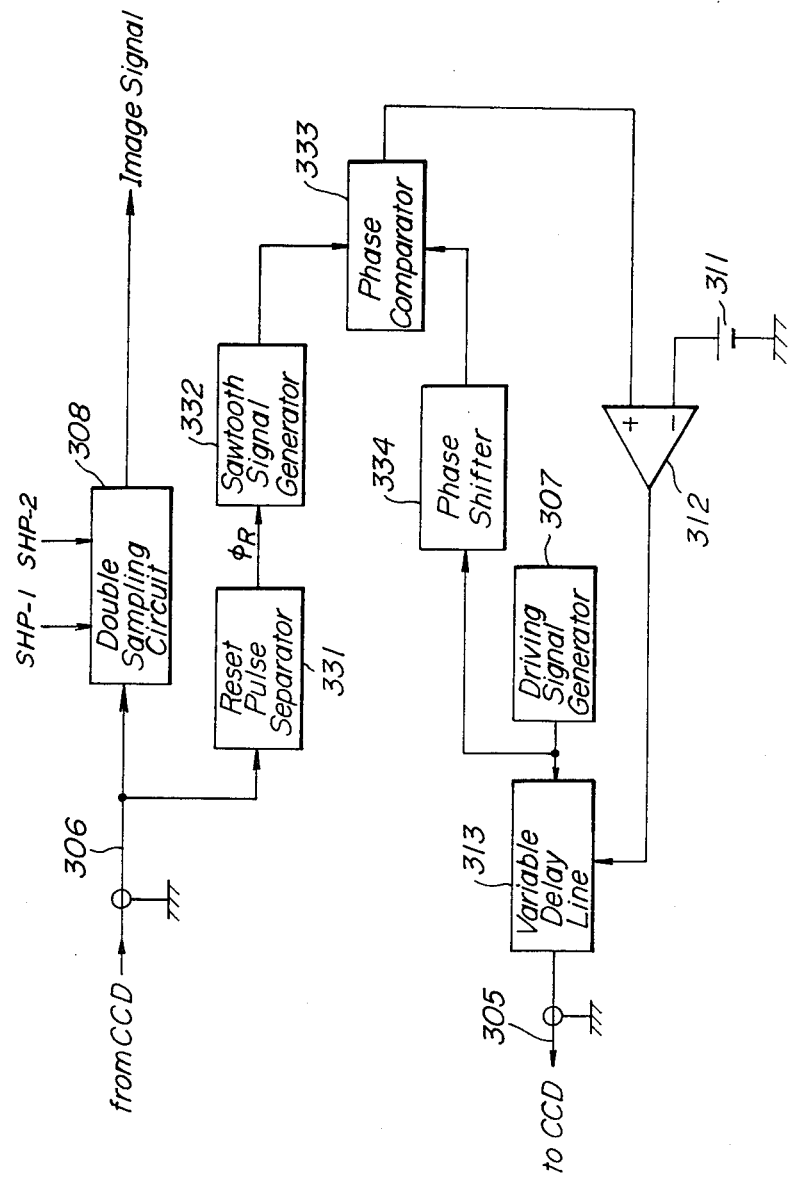

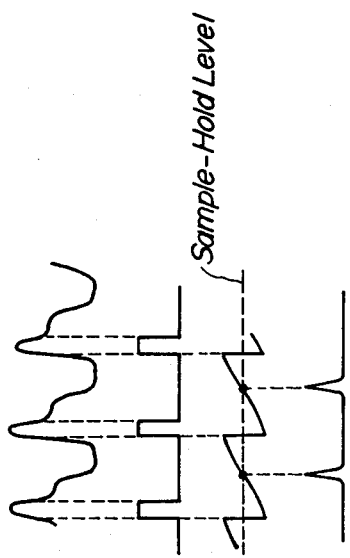
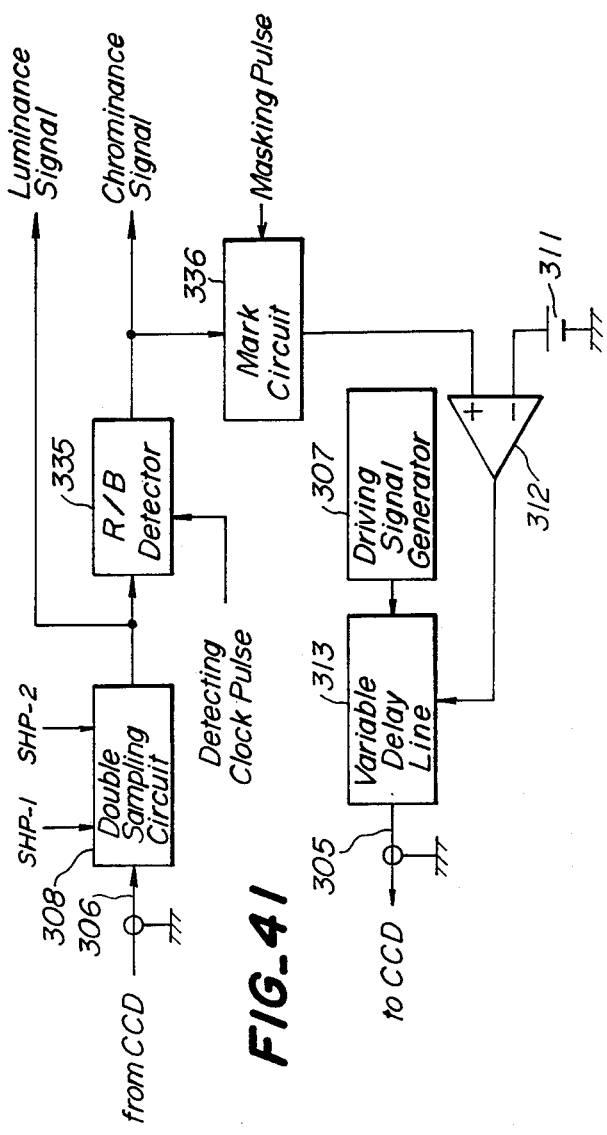
FIG_40A
FIG_40B
FIG_40C
FIG_40D
FIG_41

FIG_42A
FIG_42B
FIG_42C
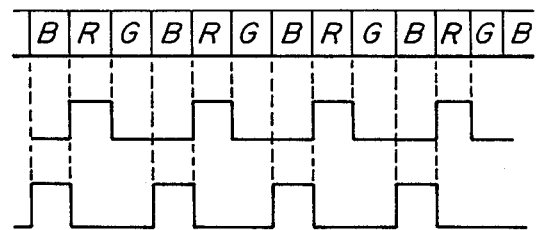
FIG_43
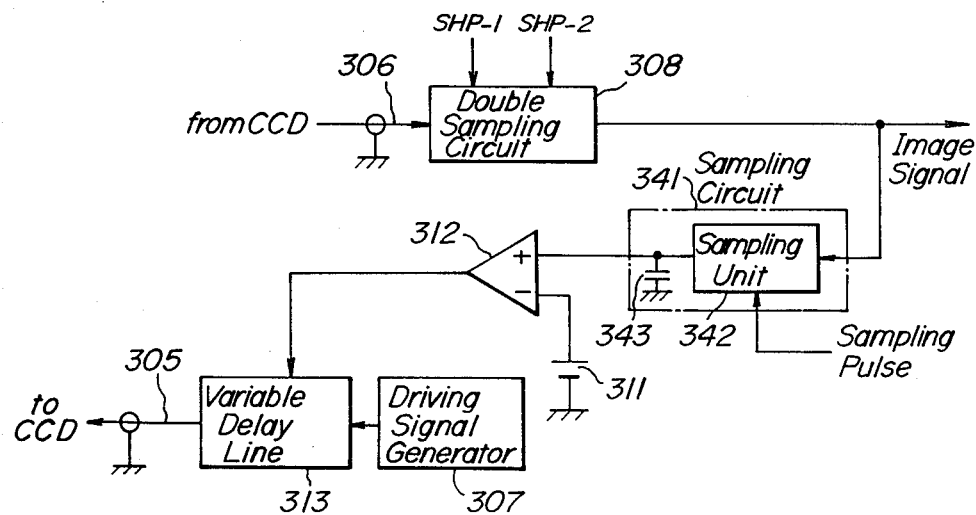

FIG._44A
FIG._44B
FIG._44C
FIG._44D
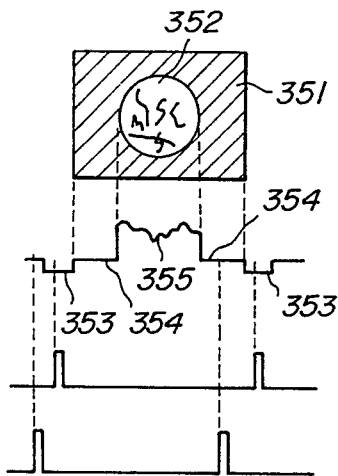
FIG._45
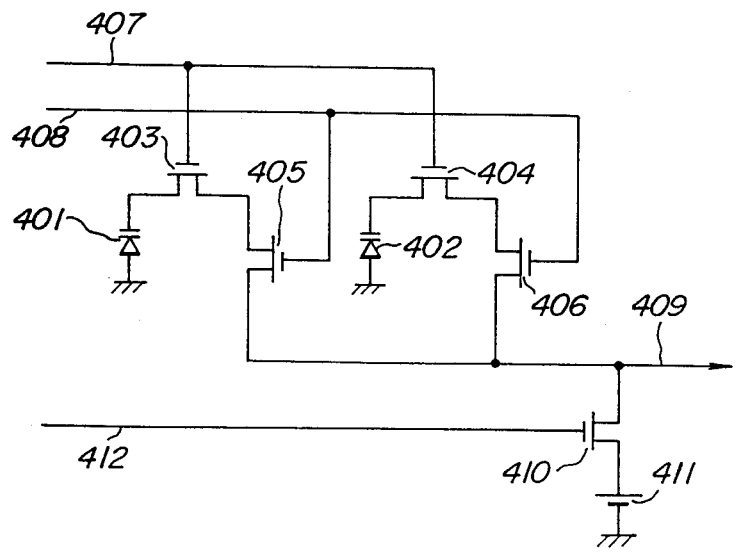

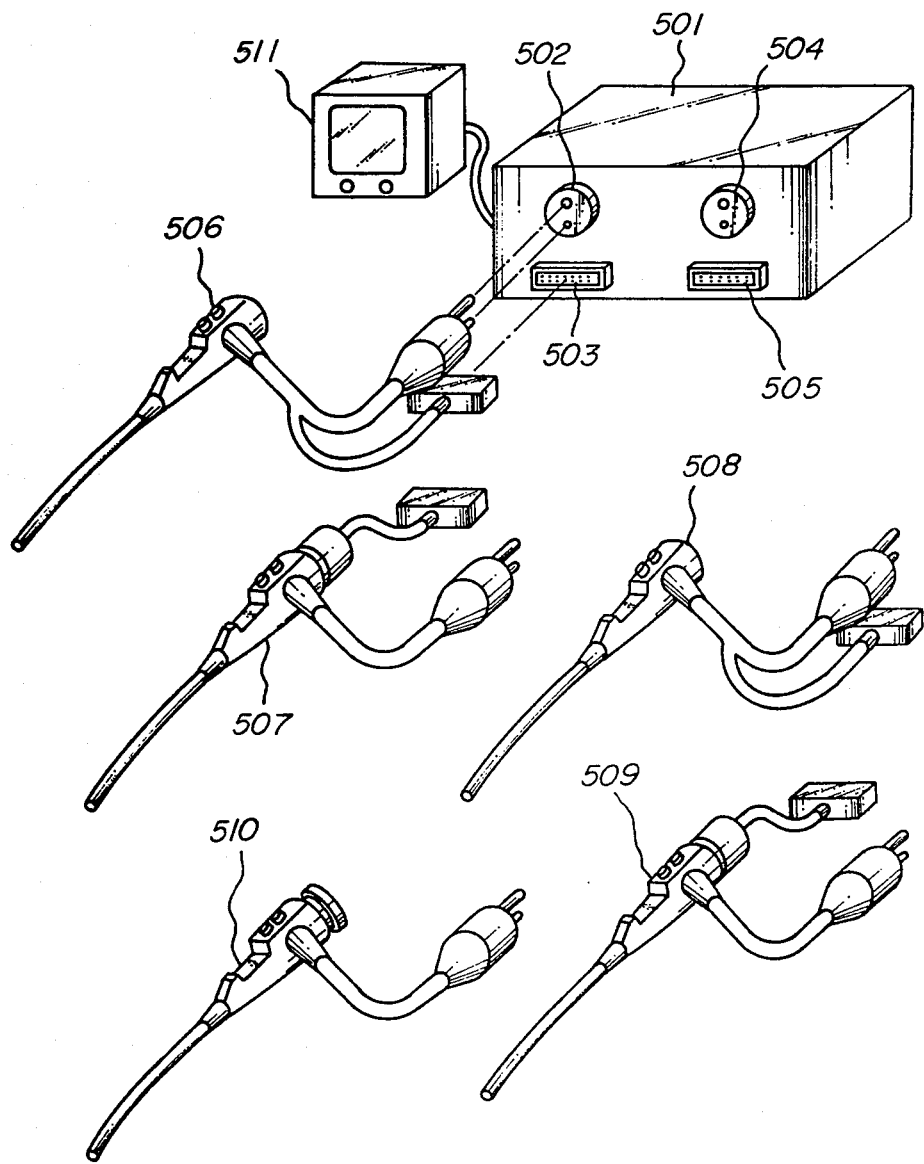
FIG_47

FIG_48
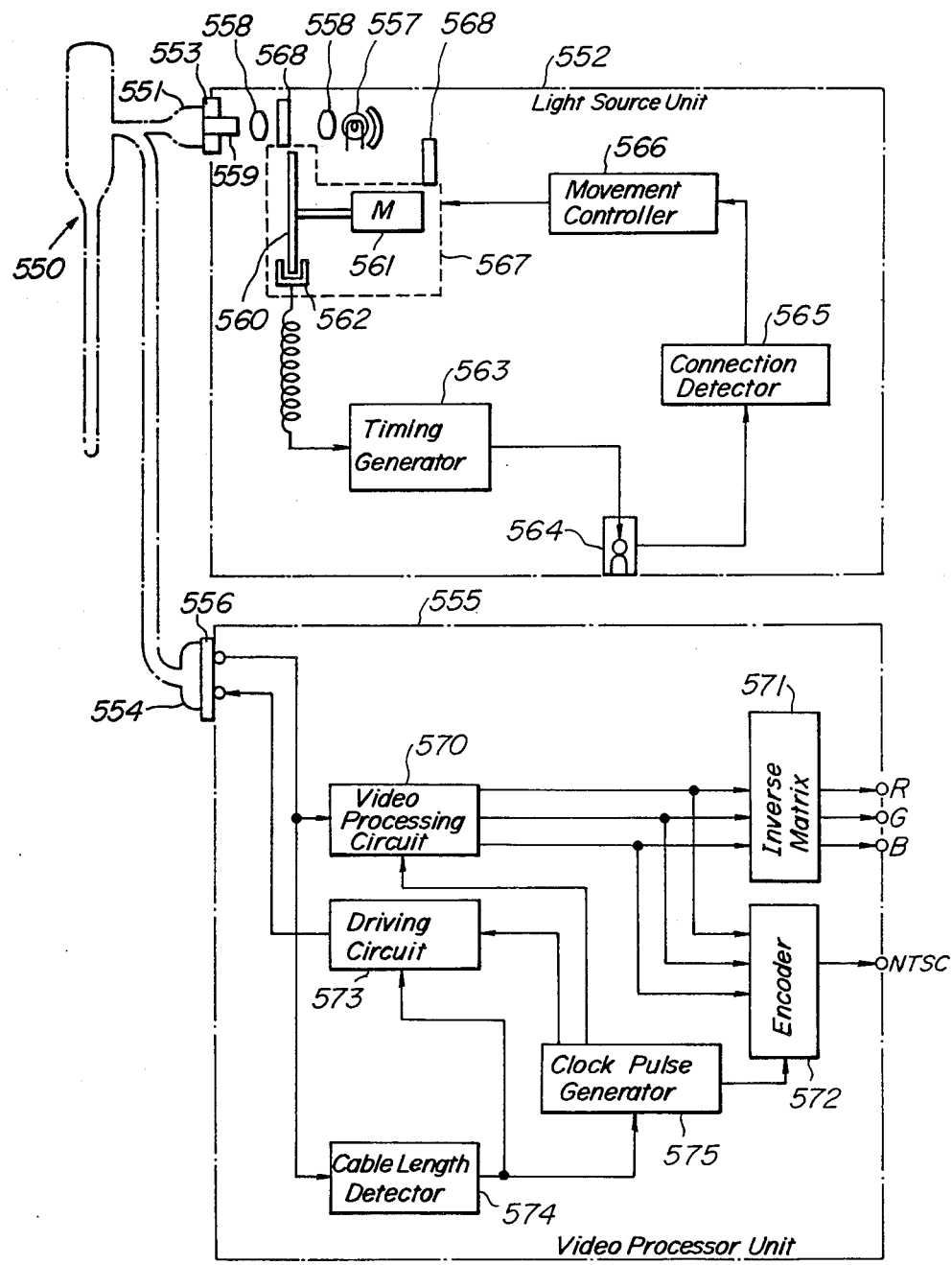

VIDEO CAMERA APPARATUS AND VIDEO ENDOSCOPE APPARATUS WITH MEANS FOR COMPENSATING IMAGE ERRORS CAUSED BY DIFFERING CABLE LENGTHS

BACKGROUND OF THE INVENTION

FIELD OF THE INVENTION AND RELATED ART STATEMENT

The present invention relates to a video camera apparatus including a camera unit having a solid state image sensor, a video processor unit for generating a driving signal for the solid state image sensor and processing an output signal from the solid state image sensor to produce an image signal, and a cable for connecting said camera unit and video processor unit to each other. This invention also relates to a video endoscope apparatus comprising the above mentioned video camera apparatus.

As is well known in the art, the video endoscope apparatus comprises a flexible insertion section having a solid state image sensor such as a CCD (charge coupled device) arranged in a distal end thereof, a video processor unit for supplying a driving signal to a CCD and processing an output signal from a CCD to derive an image signal, and a signal cable for connecting the a CCD and video processor unit to each other, the signal cable having a length of several tens of centimeters to several meters. There are many types of endoscopes for respective applications and the lengths of the cables i.e. the insertion sections differ from each other. Under such a circumstance, it is not economical to provide a plurality of video processor units for respective endoscopes, so that it is desired to use a single video processor unit commonly for a plurality of endoscopes. When the cable has a long length, amplitude, D.C. level and phase of the driving signal which is supplied from the video processor unit to the CCD via the cable as well as amplitude and phase of the signal which is transmitted from the CCD to the video processor unit also via the cable vary for respective endoscopes, so that it becomes impossible to detect the image signal under the optimum conditions.

FIG. 1 is a schematic view illustrating the known video endoscope apparatus. In a distal end of an insertion section 601, there is arranged a camera unit 603 including a CCD 602. The camera unit 603 is coupled with a video processor unit 604 arranged outside the insertion section 601 by means of coaxial cable lines 605 and 606. The video processor unit 604 comprises a driving signal generator 607 for producing a driving signal for CCD 602, a double sampling circuit 608 for sampling an output signal from a CCD 602 to derive an image signal, and a synchronizing detection circuit 609 for deriving a color image signal. These circuits 607, 608 and 609 are operated in synchronism with each other. The driving signal supplied from the driving signal generator 607 via the cable line 605 contains horizontal transfer signal $\phi_H$, charge reset signal $\phi_R$, etc. In the present invention, among these signals, the transfer signal $\phi_H$ and reset signal $\phi_R$ are important, so that the explanation of the remaining signals is omitted. The output signal supplied from a CCD 602 to the video processor unit 604 via the cable line 606 has a waveform shown in FIG. 2A. This output signal contains a reset pulse portion $S_A$ which is produced by gating the output signal of a CCD, a feedthrough portion $S_B$ which has a level independent upon an amount of incident light, and an information signal portion $S_C$ whose level is changed in accordance with an amount of incident light as illustrated by a double-headed arrow. In the double sampling circuit 608, the feedthrough portion $S_B$ is sampled by means of a first sampling signal SHP-1 illustrated in FIG. 2B and the information signal portion $S_C$ is sampled with the aid of a second sampling signal SHP-2, and then a difference between sampled values is derived as an output image signal.

FIG. 3 is a circuit diagram showing the construction of the double sampling circuit 608. The circuit 608 comprises a first field effect transistor (FET) 608a which is driven by the first sampling signal SHP-1, a first capacitance 608b for holding a value sampled by the FET 608a, a second FET 608c driven by the second sampling signal SHP-2, a second capacitance 608d for holding a value sampled by FET 608c, and a differential amplifier 608e for deriving a difference between the values held by the capacitances 608b and 608d. By using the double sampling circuit having the above mentioned construction, it is possible to reduce or cancel $1/f$ noise etc. which might be produced by an amplifier for converting an amount of charges stored in a CCD into a voltage.

As explained above, in the known video endoscope apparatus, the first and second sampling signals SHP-1 and SHP-2 which define sampling instances are synchronized with the driving signal for a CCD 602, and this phase relationship is not changed even if the cable lines 605, 606 have different lengths. However, in practice, the phase of the signal supplied from the CCD 602 to the double sampling circuit 608 varies in accordance with the length of cables. For instance, when the cable has a longer length, a time delay of the signal becomes larger, so that the signal supplied from a CCD 602 changes from a waveform shown by a solid line in FIG. 4A to a waveform illustrated by a broken line. Then, the first sampling signal SHP-1 is generated at a timing outside the feedthrough portion $S_B$ and comes into the reset pulse portion $S_A$, so that the value sampled by the first FET 608a no longer represents the level of the feedthrough portion $S_B$. This results in that the output image signal from the differential amplifier 608e does not correspond to the amount of incident light and that the image reproduced by such an image signal does not have a high image quality.

In a color television camera apparatus in which a color mosaic filter is provided on the solid state image sensor, the color information is obtained in the form of a carrier wave, so that the color information is generally derived by means of the synchronizing detection. As stated above, when the phase of the output signal from a CCD 602 becomes uncertain, firstly the sampling timing in the double sampling circuit 608 becomes uncertain, and secondly the timing of the synchronizing detection for detecting the color information becomes uncertain. That is to say, the output signal of the double sampling circuit 608 contains a carrier including the luminance signal information and a carrier having the color signal information, and the synchronous detection circuit 609 detects the color information with the aid of a synchronous detection signal. This synchronous detection signal is supplied from the driving signal generator 607. As explained above, the first and second sampling signals SHP-1 and SHP-2 for the double sampling circuit 608 are synchronized with the driving signal, e.g. the reset pulse for driving the a CCD 602 and this phase relationship is determined suitable for an endoscope having a standard cable length. Therefore, when the length of cable is different from the standard cable length, the sampling timing and synchronous detection timing deviate from optimum timings.

Further, the cable has the electrostatic capacitance and D.C. resistance, so that when the length of the cable becomes longer, high frequency components of the reset pulse are lost as shown in FIG. 5B and a period $t_H$ during which the reset pulse has an effective high level becomes shortened and the duty cycle of the reset pulse changes. Moreover, due to the D.C. resistance of the cable and the input impedance of the a CCD, the pulse high level $\phi_{RH}$ is reduced to $\phi_{RH}$-$\Delta V$ and the pulse low level $\phi_{RL}$ is increased to $\phi_{RL}+\Delta V$ as depicted in FIG. 5C. This results in that the pulse peak value is reduced and the D.C. level of the pulse is increased. Therefore, the ideal driving signal shown in FIG. 5A is no longer supplied to the CCD, so that the CCD could not operate correctly and there might be produced errors in transferring and reading out charges.

Further, due to the frequency characteristic (response characteristic) of the reading out mechanism of the CCD and the electrostatic capacitance of the cable, the reset period $t_{RA}$ Can be obtained normally under the low intensity of incident light as shown in FIG. 6A, but when the incident light has a high intensity, the signal could not raise sharply and a reset period $t_{RB}$ becomes shorter than the normal value $t_{RA}$ as illustrated in FIG. 6B, so that the image signal could not be read out correctly.

In order to avoid the above mentioned drawbacks, in Japanese Patent Publication Kokai No. 60-80,429 and U.S. Pat. No. 4,539,586 there has been disclosed a video endoscope apparatus in which means for adjusting levels of signals supplied from the video processor unit to CCD and vise versa is provided within a connector for connecting the cable between the video endoscope and the video processor unit. However, this solution has another drawback in that the connector becomes complicated in construction and expensive in cost, so that the whole system becomes expensive. Moreover, the above mentioned publications do not suggest any measures for compensating the phase deviation due to the cable length variation.

In order to mitigate the above mentioned drawbacks, in the Japanese Patent Publication Kokai No. 62-82,782 there is described a television camera apparatus in which in addition to the cable for transmitting the driving signal to the CCD and the cable for supplying the image signal read out of the CCD to the video processor unit there is arranged a third cable for transmitting a driving pulse for reading the image signal from the CCD and the image signal read out of the CCD is sampled with the aid of the driving pulse. In Japanese Patent Publication Kokai No. 61-29,584, there is described the television camera apparatus comprising an additional control cable between the camera unit and the video processor unit and a current having a constant amplitude passes through the control cable and a voltage drop thereacross is detected. Then the detected voltage drop is compared with a reference voltage to detect a length of the cable and the decay of the high frequency components due to the cable is compensated for. Further, in Japanese Patent Publication Kokai No. 62-120,794, there is disclosed a television camera apparatus which includes a third control cable, a means for transmitting a monitor signal from the video processor unit to the camera unit, and a means for transmitting the output signal read out of the CCD together with the received monitor signal to the video processor unit. In the video processor unit, the transmitted and received monitor signal is extracted and its level is compared with a reference level, and a transmission distortion is compensated for in accordance with the output of the comparator. In these known television camera apparatuses, there is arranged the control cable in addition to the driving signal transmission cable and the image signal transmission cable, so that the construction of the cable system becomes complicated. Particularly, in the video endoscope apparatus, a diameter of the insertion section has to be made small as far as possible, so that it is practically difficult to provide the third cable within the insertion section.

In Japanese Patent Publication Kokai No. 61-187,470, there is described another television camera apparatus in which the reset pulse portion contained in the output signal supplied from the CCD to the video processor unit is extracted and a sampling pulse is generated by a phase locked oscillator which is phase-locked with the extracted reset pulse portion. However, in this television camera apparatus, it is possible to compensate the time delay introduced in the signal path from the CCD to a sample-hold circuit in the video processor unit, but it is impossible to compensate the decay in this signal path and the decay and delay introduced in the signal path from the video processor unit to the camera unit, so that it is practically difficult to obtain the image having the high quality.

In Japanese Patent Publication Kokai No. 61-147,680, there is described still another television camera apparatus in which the reset pulse contained in the output signal from the CCD is extracted in the video processor unit, its amplitude is compared with a reference value and an amplitude of the reset pulse contained in the driving signal for the CCD is adjusted in accordance with a result of the comparison. In this apparatus, the phase deviation due to the delay time introduced by the cable from the camera unit to the video processor unit could not be compensated for at all, so that the image signal could not be obtained correctly.

In Japanese Patent Publication Kokai No. 62-77,935, there is proposed a television camera apparatus in which the camera unit comprises a high frequency oscillator and an output high frequency signal therefrom is superimposed upon the output signal read out of the CCD, and in the video processor unit, the high frequency signal is extracted to detect the cable length in accordance with the detected level of the high frequency signal and the gain of the signal transmitted from the camera unit is controlled in accordance with the detected cable length. However, this television camera apparatus has a drawback that the high frequency oscillator has to be installed in the camera unit, so that the camera unit becomes complicated and large. This results in that the apparatus could not be applied to the video endoscope apparatus.

SUMMARY OF THE INVENTION

The present invention has for its object to provide a novel and useful video camera apparatus and video endoscope apparatus, in which the deterioration of the image quality due to the deviations of the delay time, signal level and effective reset period which are caused by the difference in the cable length can be avoided by means of the simple construction.

According to the invention, a video camera apparatus comprises a camera unit having a solid state image sensor for converting an optical image of an object into an electric signal;

a video processor unit including a driving circuit for generating a driving signal for driving the solid state image sensor, and a video processing circuit for processing the electric signal supplied from the solid state image sensor to derive an image signal;

a signal cable connected between the camera unit and the video processor unit and including a first signal line for transmitting said driving signal from the video processor unit to the camera unit and a second signal line for transmitting the electric signal supplied from the solid state image sensor from the camera unit to the video processor unit; and a cable length detetion circuit provided in said video processor unit for processing the electric signal transmitted from the solid state image sensor via the second signal line of said cable to derive cable length information representing the length of the signal cable.

In a preferred embodiment of the video camera apparatus according to the invention, the video processor unit comprises means for modulating the driving signal for the solid state image sensor in accordance with a modulation signal, means for demodulating a modulated component contained in the output signal from the solid state image sensor, means for comparing a phase of an output signal from the demodulating means with a phase of said modulation signal to derive the information about the length of the cable, and means for automatically adjusting a phase of said driving signal in accordance with the detected information about the length of the cable.

In another preferred embodiment of the video camera apparatus according to the invention, the video processor unit comprises means for modulating the driving signal for the solid state image sensor in accordance with a modulation signal, means for demodulating modulated components contained in the output signal supplied from the solid state image sensor, means for comparing a phase of an output signal from the demodulating means with a phase of said modulation signal to derive information representing the length of the cable, and means for automatically adjusting at least one of peak value and D.C. level of the driving signal in accordance with the detected information about the length of the cable.

In the video camera apparatus according to the invention, the information representing the length of the cable is detected from the output signal supplied from the solid state image sensor, and at least one of the phase, peak value and D.C. level of the driving signal is adjusted in accordance with the detected cable length. Therefore, even if the delay time and level of the signal are varied due to the difference in the cable length, it is always possible to obtain the image signal correctly. Further, since it is not necessary to provide the member of identifying the cable length in the cable connector, the connector can be constructed simply. Particularly, in the preferred embodiment of the video camera apparatus according to the invention, in which the driving signal is modulated and the output signal from the solid state image sensor is demodulated to detect the cable length, the detection of the cable length can be carried out precisely without being affected by noise, and therefore the driving signal can be corrected even under the worse condition with great noise and on image having high quality can be reproduced.

According to further aspect of the invention, a video endoscope apparatus comprises an insertion section insertable into an object under inspection;

a solid state image sensor arranged at a distal end of the insertion section for converting an optical image of the object into an electric signal;

a video processor unit having a driving circuit for generating a driving signal for the solid state image sensor and a video processing circuit for processing the electric signal supplied from the solid state image sensor to derive an image signal;

a signal cable arranged within the insertion section and including a first signal line for transmitting the driving signal supplied from the driving circuit to the solid state image sensor and a second signal line for transmitting the electric signal supplied from the solid state image sensor to the video processing circuit;

a code accommodating said first and second signal lines and having one end connected to a proximal end of the insertion section and the other end connectable to the video processor unit by means of a connector;

a display device for displaying the image signal processed by the video processing circuit; and a cable length detection circuit provided in said video processor unit for processing the electric signal supplied from the solid state image sensor through the second signal line to detect cable length information representing the length of the signal cable.

BRIEF DESCRIPTION OF THE DRAWINGS

FIG. 1 is a schematic view showing the construction of the known video endoscope apparatus;

FIGS. 2A–2C are signal waveforms for explaining the operation of the apparatus shown in FIG. 1;

FIG. 3 is a circuit diagram illustrating the construction of a double sampling circuit of the apparatus of FIG. 1;

FIGS. 4A–4C are signal waveforms for explaining the operation of the double sampling circuit;

FIGS. 5A–5C are waveforms for depicting the variation of the reset signal;

FIGS. 6A and 6B are signal waveforms for showing the variation in the effective reset period;

FIG. 7 is a schematic view showing the principal construction of an embodiment of the video endoscope apparatus according to the invention;

FIG. 8 is a schematic view illustrating the whole construction of the apparatus shown in FIG. 7;

FIG. 13 is a block diagram depicting still another embodiment of the video endoscope apparatus according to the invention;

FIG. 14 is a block diagram illustrating another embodiment of the video processing circuit;

FIG. 15 is a block diagram showing an embodiment of the video camera apparatus according to the invention;

FIGS. 16A–16C, 17A–17C and 18A–18C are signal waveforms for explaining the operation of the apparatus of FIG. 15;

FIG. 19 is a frequency spectrum of the output signal from CCD;

FIGS. 20A and 20B are signal waveforms for explaining the synchronous detection;

FIG. 21 is a block diagram showing another embodiment of the video processor unit according to the invention;

FIGS. 23A and 23B are signal waveforms for explaining the operation of the apparatus shown in FIG. 22;

FIGS. 26A and 26B are signal waveforms for explaining the operation of the apparatus illustrated in FIG. 25;

FIG. 28 is a schematic view for explaining the operation of the apparatus of FIG. 27;

FIG. 29 is a circuit diagram showing the feedback loop of the apparatus of FIG. 27;

FIGS. 34 and 35 are graphs showing characteristics of the gain control amplifier of the apparatus shown in FIG. 33;

FIG. 36 is a circuit diagram illustrating another embodiment of the gain control amplifier;

FIG. 37 is a block diagram depicting still another embodiment of the video endoscope apparatus according to the invention;

FIG. 39 is a block diagram illustrating another embodiment of the video processor unit according to the invention;

FIGS. 40A–40D are signal waveforms for explaining the operation of the video processor unit shown in FIG. 39;

FIG. 41 is a block diagram depicting still another embodiment of the video processor unit according to the invention;

FIGS. 44A–44D are a schematic view nd signal waveforms for explaining the operation of the video processor unit of FIG. 43;

FIG. 45 is a circuit diagram illustrating another embodiment of the solid state imager sensor of the television camera apparatus according to the invention;

FIG. 47 is perspective view illustrating various combinations of a plurality of video endoscopes and a video processor unit; and FIG. 48 is a block diagram depicting still another embodiment of the video endoscope apparatus according to the invention.

DESCRIPTION OF THE PREFERRED EMBODIMENTS

Figure 9:
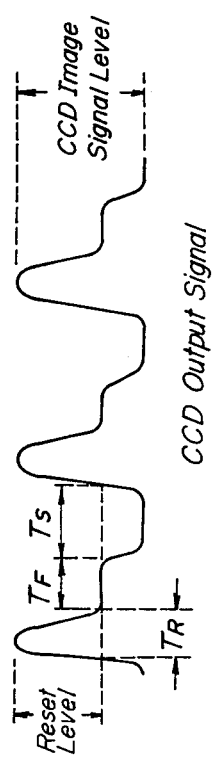
FIG. 9 is a waveform of the output signal from CCD.
Figure 10:
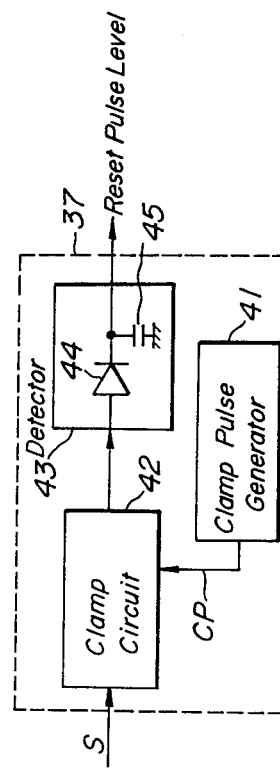
FIG. 10 is a circuit diagram representing the construction of the reset pulse level detector of FIG. 8.
Figure 11:
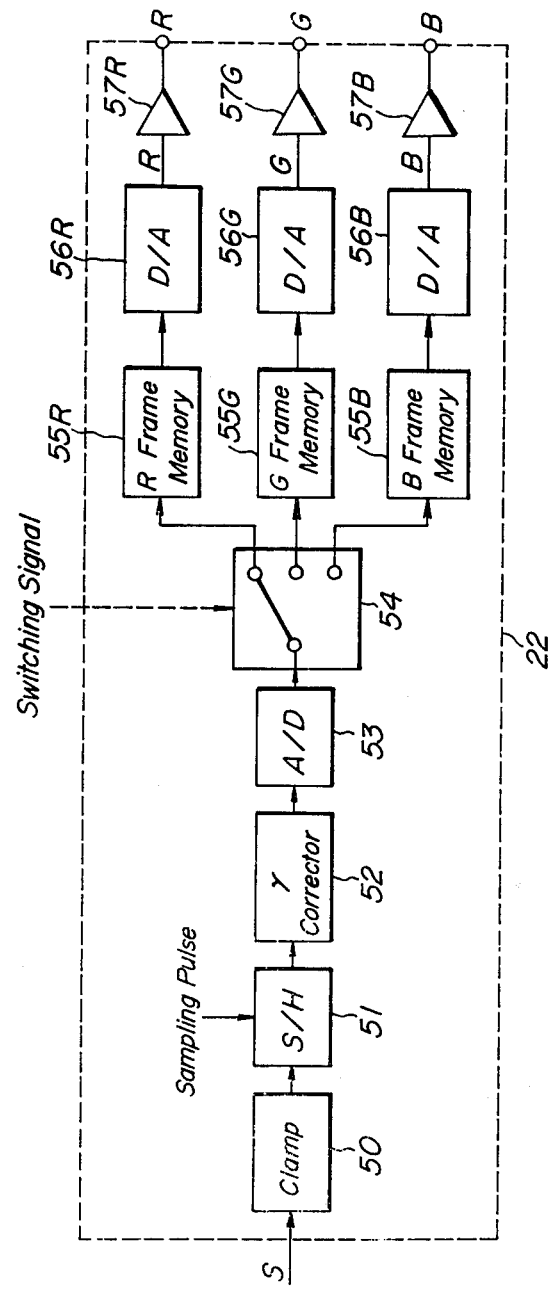
FIG. 11 is a block diagram illustrating the construction of the video processing circuit shown in FIG. 8.

FIGS. 7–11 show a first embodiment of the video endoscope apparatus according to the invention. FIG. 7 illustrates the construction of a major portion of the video endoscope apparatus, FIG. 8 the whole construction thereof, FIG. 9 a waveform of an output signal of the CCD, FIG. 10 the construction of a reset pulse level detector, and FIG. 11 is a block diagram illustrating a video processing circuit.

As shown in FIG. 8, the video endoscope apparatus 1 comprises a video endoscope 3 having an insertion section 2, a video processor unit 5 having a connector 4 for receiving the video endoscope 3 and signal processing circuits, and a color monitor 6 for receiving the image signal supplied from the video processor unit 5 to display a color image of an object.

The video endoscope 3 includes the thin insertion section 2 which is insertable into cavities of human bodies and pipes of mechanical constructions, an operation section 7 connected to a proximal end of the insertion section 2, the operation section having such shape and dimension that an operator can be positively and easily grasp the operation section, and a universal cord 8 extending from the operation section.

At a distal end of the insertion section 2 are arranged an objective lens 9 which forms an optical image of the object and a solid state image sensor 11 which receives the optical image of the object and converts it into an electric signal. In the present embodiment, the solid state image sensor 11 is constituted by a charge coupled device and will be called CCD hereinafter. The objective lens 9 and CCD 11 form the image picking up means for producing the electric signal representing the image of the object under inspection.

In the insertion section 2 there is arranged a light guide 13 for transmitting illumination light therethrough. The light guide 13 is extended through the universal cord 8 and its light entrance end is faced to a light source 14 by means of the connector 4. In this manner, the light transmitted through the light guide 13 can illuminate the object to be picked up by the objective lens 9 and CCD 11.

In the insertion section 2 and universal cord 8, there is also inserted a signal cable 15 which is coupled with the video processor unit 5 by means of the connector 4 and a socket 16, so that the signal transmission can be effected between the video endoscope 3 and the video processor unit 5. The video processor unit 5 comprises a clock generator 17 for generating a clock signal and a CCD driver circuit 18 which produces a CCD driving signal in synchronism with the clock signal. The driver circuit 18 includes a reset pulse and horizontal transfer pulse generator 19 and a vertical transfer pulse generator 20, and generates charge reset pulse $\phi_R$, horizontal transfer vertical transfer pulse $\phi_V$.

The vertical transfer pulse $\phi_V$ is supplied to the CCD 11 via a first signal line 15a of the cable 15, and the reset pulse $\phi_R$ and horizontal transfer pulse $\phi_H$ generated by the reset pulse and horizontal pulse generator 19 are supplied via a driving condition control circuit 21 and the first signal line 15a to the CCD 11 as illustrated in FIG. 7. Under the control of the driving signal supplied from the driver circuit 18, the CCD 11 generates an output electric signal S and the signal S is supplied via the second signal line 15b of the cable to a video processing circuit 22 and the driving condition control circuit 21. The video processing circuit 22 processes the output signal S from the CCD 11 to derive an image signal which is displayed on the color monitor 6.

In the video endoscope apparatus of the present embodiment, the color image is picked up in the field or frame sequential television system, and thus the light source 14 comprises a lamp 31 for emitting white light, a rotary filter 33 driven by a motor 32 and having red, green and blue color filter sections, and a lens 34 for focusing the light onto the incident end face of the light guide 13.

As shown in FIG. 7, the driving condition control circuit 21 comprises a gain control amplifier (abbreviated as GCA) 36 for receiving the reset pulse $\phi_R$ and horizontal transfer pulse $\phi_H$ from the generator 19, a reset pulse level detector 37 for detecting a level of the reset pulse portion of the output signal S from the CCD 11, and a differential amplifier 39 for comparing the detected reset pulse level $S_{PR}$ with a reference voltage $V_{REF}$ given by a reference voltage source 38 to derive a difference signal therebetween. The difference signal is then supplied to a gain control terminal of the GCA 36 so that the amplitude of the reset pulse $\phi_R$ and horizontal transfer pulse $\phi_H$ is adjusted in accordance with the difference signal.

To the reset pulse level detector 37 is supplied the output signal S form the CCD 11. As shown in FIG. 9 this signal S has a varying level in accordance with the length of the cable 15. That is to say, the longer the cable 15 is, the larger the loss is, and thus the signal level becomes smaller. The signal S is composed of a reset pulse period $T_R$, a feedthrough period $T_F$ and a signal period $T_s$, and the reset pulse level $L_R$ in the reset pulse period $T_R$ becomes smaller in pro portion to the length of the cable 15. The reset pulse level $L_R$ becomes equal to the output level of the generator 19 if the cable length is zero, and the reset pulse level $L_R$ becomes smaller by the loss due to the length of the cable 15. Therefore, by detecting the reset pulse level $L_R$ of the output signal S received via the cable 15, it is possible to detect the Cable length or the loss amount due to the cable 15.

Therefore, the level of the reset pulse $\phi_R$ and horizontal transfer pulse $\phi_H$ before the transmission through the cable 15 is made large in accordance with the detected loss, the level of these pulses received at the CCD 11 becomes equal to the standard or nominal level and the level of the signal S received at the video processor unit is made constant regardless of the length of the cable 15. In this manner, the CCD 11 can be driven optimally and the image signal having high image quality can be obtained.

FIG. 10 is a circuit diagram illustrating the construction of the reset pulse level detector 37 for detecting the reset pulse level at the video processor unit 5.

The output signal S from the CCD 11 is supplied to a clamp circuit 42 to which a clamp pulse CP generated by a clamp pulse generator 41 is also supplied. The clamp circuit 42 serves to clamp the level of the feedthrough portion of the signal S to a given DC clamp level. This clamping operation is carried out under the control of the clamp pulse CP which is generated at a timing corresponding to the feedthrough period $T_F$. This is similar to the known direct current regeneration circuit for clamping the pedestal level. An output signal from the clamp circuit 42 is detected by a diode 44 serving as a detecting element of a detection circuit 43. A peak value of the detected output, i.e. the peak value of the reset pulse is held in a capacitance 45. The output signal from the detection circuit 43 is supplied to the differential amplifier 39 as shown in FIG. 7 and is compared with the reference voltage $V_{REF}$. Then, the difference produced by the differential amplifier 39 is applied to the GCA 36 to control its gain. In this manner, the CCD 11, reset pulse level detector 37, differential amplifier 39 and gain control amplifier 36 constitute a feedback loop by means of which the peak value of the reset pulse is automatically adjusted to be equal to the reference voltage $V_{REF}$. Therefore, the level of the reset pulse $\phi_R$ and horizontal transfer pulse $\phi_H$ becomes constant regardless of the length of the cable 15, and thus the CCD operates always correctly and the level of the output image signal of the CCD is adjusted to a desired value.

FIG. 11 is a block diagram illustrating the construction of the video processing circuit 22. The output signal S from the CCD 11 is supplied via the signal line 15b to the video processor unit 5 and is clamped by a clamp circuit 50. Then, an output signal from the clamp circuit 50 is supplied to a sample/hold circuit 51 in which the image signal during the image signal period $T_s$ is sampled and held. Then, the $\gamma$ correction is effected by a $\gamma$ corrector 52 and is converted into a digital signal by means of an A/D converter 53. Further, the digital signal supplied to a multiplexer 54 which is driven by a switching signal synchronized with the rotation of the rotary filter 33 and generated by a timing generator not shown. In this manner, the image signals picked up by red, green and blue illumination lights are successively stored in R, G and B frame memories 55R, 55G and 55B, respectively. The image signals stored in these memories 55R, 55G and 55B are read out simultaneously and are converted into red, green and blue color signals R, G and B by means of D/A converters 56R, 56G and 56B, respectively. These color signals are supplied via buffer amplifiers 57R, 57G and 57B to the color monitor 6.

It should be noted that the color signals R, G and B may be supplied to a matrix circuit to derive luminance signal Y and color difference signals R-Y, G-Y and then these signals may be supplied to NTSC encoder to derive a composite color television signal.

In the above mentioned first embodiment, an amount of the loss or decay due to the signal cable 15 is detected by the reset pulse level detector 37 and the level of the driving signal for the CCD is adjusted in accordance with the detected decay, so that the level of the output signal supplied from the CCD and received at the video processor unit can be set to a desired level regardless of the length of the cable. Therefore, it is not necessary to provide the level adjusting means for adjusting the image signal level for respective video endoscopes or to adjust the level of the output signal from the level adjusting means, and therefore the construction becomes simple and the variation for respective video endoscopes can be easily restricted within a given range so that the apparatus having high quality can be proposed.

Figure 12:
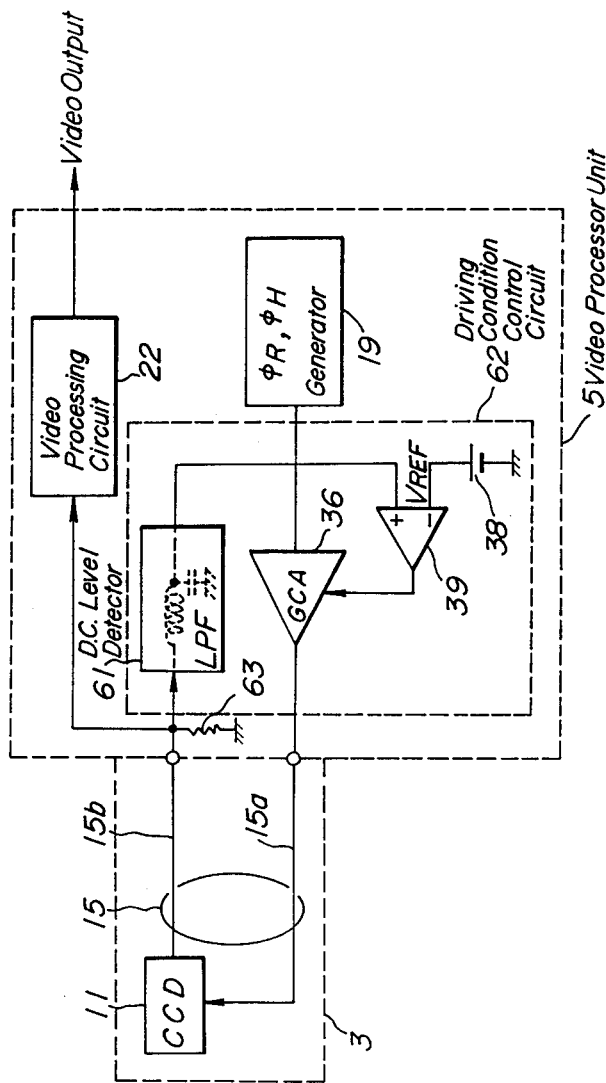
FIG. 12 is a block diagram showing the principal construction of another embodiment of the video endoscope apparatus according to the present invention.

FIG. 12 is a block diagram illustrating a major portion of a second embodiment of the video endoscope apparatus according to the invention.

The present embodiment differs from the first embodiment shown in FIG. 7 in the point that a D.C. level detector 61 instead of the reset pulse detector 37 is provided in a driving condition control circuit 62. The D.C. level detector 61 detects a D.C. level of the output signal S supplied from the CCD 11 via the second signal line 15b of the cable 15 and its input is connected to the ground potential via a resistor 63.

The present embodiment is constructed on the basis of the recognition of the fact that the signal cable 15 has a D.C. resistance component which is increased in proportion to the length of the cable 15, so that the cable length can be detected by measuring the resistance value.

In general, the output signal from the CCD 11 has a D.C. bias level applied thereto. When it is assumed that the D.C. bias voltage is represented by $E_b$, the resistance value of the resistor 63 is expressed by R63 and the resistance value of the signal cable 15 is denoted by R15. Then, across the resistor 63 there is generated a voltage represented by $E_b \times R63/R15$. This voltage is applied to the D.C. level detector 61 and only the D.C. component is extracted. That is to say, in order to remove the image signal component in the output signal of the CCD 11, the D.C. level detector 61 includes a low pass filter (LPF) composed of a coil and a capacitor. The output signal of the D.C. level detector 61 is applied to one input of the differential amplifier 39 and is compared with the reference voltage $V_{REF}$ generated by the reference voltage source 38 and applied to the other input of the differential amplifier 39. The difference signal from the differential amplifier 39 is applied to the gain control terminal of the gain control amplifier 36 so that the amplitude of the reset pulse $\phi_R$ and horizontal transfer pulse $\phi_H$ generated by the reset pulse and horizontal transfer pulse generator 19 is adjusted.

The remaining construction of the apparatus shown in FIG. 12 is similar to that of the first embodiment and portions which are same as those of the first embodiment are denoted by the same reference numerals used in the first embodiment.

In this embodiment, the CCD 11, D.C. level detector 61, differential amplifier 39 and GCA 36 constitute an open loop control circuit. Therefore, the GCA 36 operates to make larger the level of the reset pulse $\phi_R$ and horizontal transfer pulse $\phi_H$ when the cable 15 becomes longer, so that the level of the reset pulse and horizontal transfer pulse supplied to the CCD 11 can be remained constant regardless of the length of the cable 15, and the CCD 11 can be always driven optimally.

FIG. 13 is a block diagram showing a third embodiment of the video endoscope apparatus according to the invention. In the present embodiment, in addition to the signal cable including the first and second signal lines there is provided a dummy line 71. By detecting a voltage drop due to the dummy line 71, the driving condition for the CCD 11 can be controlled. To the CCD 11, a power supply voltage $V_{cc}$ is applied via a power supply line 73. A video endoscope 3' of this embodiment may be used for inserting a small electric knife therethrough. In this case, a large A.C. current is supplied to the electric knife, so that the A.C. current might be induced by means of the static induction or electromagnetic induction into a signal line 74 for supplying the output signal from the CCD 11 to the video processor unit 5. In this embodiment, the induction of the A.C. current for the electric knife is detected by detecting the signal supplied from the dummy line 71 and the detected induced signal is subtracted from the output signal supplied through the signal line 74 to cancel the influence of the induction of the A.C. current for the electric knife.

In the third embodiment, a distal end of the dummy line 71 is connected via a resistor 75 to a power supply terminal of the CCD 11 to which the power supply voltage $V_{cc}$ is applied. The proximal end of the dummy line 71 is connected to the ground via a resistor 76 provided in the video processor unit 5 as well as to an input of a D.C. level detector 77.

The D.C. level detector 77 detects the voltage drop due to the dummy line 71 to measure the length of the signal cable lines 74, 78. It is now assumed that a resistance of the dummy line 71 itself is represented by $R_d$ and resistance values of the resistors 75 and 76 are expressed by R75 and R76. Then, the voltage E produced across the resistor 76 is expressed by $R_d \times V_{cc}/(R75+R_d+R76)$. This voltage E is applied to the D.C. level detector 77 and only the D.C. level thereof is detected. That is to say, the A.C. component due to the electric knife is removed. The output signal from the D.C. level detector 77 is applied to the gain control terminal of the GCA 36 to control the level of the reset pulse $\phi_R$ and horizontal transfer pulse $\phi_H$ generated from the generator 19. The driving signal from the GCA 36 is supplied to the CCD 11 via the second signal line 78.

In the manner explained above, the resistor 75, dummy line 71, resistor 76, D.C. level detector 77 and GCA 36 constitute the open loop automatic control which operates to keep the reset pulse $\phi_R$ and horizontal transfer pulse $\phi_H$ at a given level even if the length of the cables of respective video endoscopes differ from each other so that the CCD 11 is driven under the optimum condition.

In the second and third embodiments, instead of using the video processing circuit 22, use may be made of a video processing circuit 82 including an automatic gain controller 81 whose gain is controlled in accordance with the detected cable length and then the output signal of the automatic gain controller may be supplied to the clamp 50. In this case, it is possible to remove the variation of the image signal level due to the difference in the cable length.

In the embodiments so for explained, the level of the reset pulse $\phi_R$ and horizontal transfer pulse $\phi_H$ is adjusted in accordance with the detected cable length, but the level of the vertical transfer pulse $\phi_v$ may be additionally adjusted, if desired.

According to the invention, the cable length is measured by detecting the output signal supplied from the solid state image sensor via the signal cable, and the condition for driving the solid state image sensor is controlled in accordance with the detected cable length such that the solid state image sensor is operated under the substantially same optimum condition.

FIG. 15 is a block diagram showing still another embodiment of the video endoscope apparatus according to the invention. A camera unit 112 provided at the distal end of an insertion section 111 has the same construction as that of the known video endoscope and comprises a solid state image sensor 113 composed of CCD. In this embodiment, a mosaic color filter is provided on a front surface of the CCD 113 to constitute the video endoscope of simultaneous television system. A video processor unit 114 comprises a driving signal generator 115 to generate reset pulse $\phi_R$ and horizontal transfer pulse $\phi_H$. The reset pulse $\phi_R$ is modulated by a phase modulator 116 and then is supplied to the CCD 113 through a cable 117. When the reset pulse $\phi_R$ is phase-modulated, the reset pulse portion contained in an output signal from the CCD 113 is correspondingly phase modulated.

FIGS. 16A to 16C show waveforms of reset pulse $\phi_R$, horizontal transfer pulse $\phi_H$ and output signal of the CCD 113. These signals are synchornized with each other. Therefore, when the reset pulse $\phi_R$ is phase-modulated, the reset pulse portion contained in the output signal of the CCD 113 is similarly phase-modulated. The horizontal transfer pulse $\phi_H$ is sent to the CCD 113 via a cable 118. The video processor unit 114 further comprises a voltage controlled oscillator (VCO) 119 for generating a clock pulse for the driving signal generator 115. In the present embodiment, the output frequency of the VCO 119 is set to 14 MHz. Repetion frequencies of the reset pulse $\phi_R$ and horizontal transfer pulse $\phi_H$ are set to 7 MHz. The output clock pulse from the VCO 119 is also supplied to a frequency divider 120 to divide the frequency of the clock pulse by 4. An output signal of the frequency divider 120 is supplied via a gate circuit 121 to the phase-modulator 116 as a modulating signal. The frequency divider 120 is constituted by a flip-flop and is reset by a horizontal synchronizing signal HD supplied from the driving signal generator 115, so that the output signal of the frequency divider 120 and the output signal of the horizontal synchronizing signal HD have the fixed phase relationship.

FIGS. 17A and 17B show the phase relationship of the horizontal synchronizing signal HD and the output signal of the CCD 113, and FIG. 17C shows the image displayed on the monitor. In the video endoscope apparatus according to this embodiment, the image of the object is not displayed on the whole monitor screen, but is displayed on a part of the monitor screen as denoted by hatchings in FIG. 17C. That is to say, as illustrated in FIG. 17B the image information is not extent in a part Ta of the output signal from the CCD and is contained only in a part Tb. In the present embodiment, the non-pictorial part Ta free from the image information is utilized to effect the phase-mudulation of the reset pulse $\phi_R$ only during this phase-modulated, the image information is not deteriorated. To this end, the horizontal synchronizing signal HD shown in FIG. 18A is supplied to a gate pulse generator 122 to generate a gate pulse shown in FIG. 18B. The time period Ta during which the gate pulse is generated corresponds to the non-pictorial area on the monitor screen. The gate circuit 121 is controlled by the thus generated gate pulse and the output of the frequency divider 120 having the frequency of 14/4 MHz is passed through the gate circuit during the gate pulse period Ta. The output signal from the gate circuit 121 is supplied to the phase-modulator 116 and the reset pulse $\phi_R$ is phase-modulated in accordance with the modulation signal having the frequency of 14/4 MHz. The output signal from the CCD 113 is supplied through a second signal line 123 to the video processor unit 114, and the reset pulse contained in this output signal is separated by a reset pulse separator 124. The reset pulse thus separated is supplied to a demodulator 125 to demodulate the phase modulated component. The phase-demodulated signal has a frequency of 14/4 MHz. The reset pulse separator 124 is formed by a voltage comparator, and its threshold potential is shown by a level $L_{DH}$ in FIG. 16C. The demodulator 125 may be composed of an FM demodulator of usual construction. In the present embodiment, the demodulator 125 is constructed by an FM demodulator of pulse count system. The output signal of the demodulator 125 is supplied to a band pulse filter (BPF) 126 having a center frequency of 14/4 MHz to extract a sinusoidal modulation component of 14/4 MHz. The output signal of BPF 126 is supplied to one input of a phase comparator 127.

The output signal from the CCD 113 is also supplied to a double sampling circuit 128 and is double-sampled by means of sampling pulses SHP-1 and SHP-2 supplied from a timing pulse generator 129, so that 1/f noise is mainly removed. The output signal of the double sampling circuit 128 is further supplied to a low pass filter (LPF) 130 to derive a luminance signal. The output signal is further supplied to a band pass filter (BPF) 131 and is then supplied to a synchronous detector 134 to derive a chrominace signal.

FIG. 19 is a graph showing a spectrum of the the output signal of the CCD having a mosaic color filter applied on its front surface. $S_1$ shows a base band of the luminance signal component and has a band width of about 2 MHz and $S_2$ shows a frequency band of a color subcarrier having a center frequency of 3.5 MHz and a frequency band width of about ±500 KHz. Therefore, the cut off frequency of LPF 130 is set to about 2.5 MHz in order to extract the luminance signal component $S_1$. BPF 131 extracts the carrier signal component $S_2$ of the chrominance signal and the synchronous detection is effected by the synchronous detector 132 to reproduce the chrominance signal. In the present embodiment, the chrominance signal is color difference signals R-Y and B-Y which are alternately generated for respective scanning lines. The luminance signal and chrominance signal are further supplied to succeeding signal processing circuits, and are converted into a composite NTSC color television signal or RGB signals which are supplied to the color monitor.

In FIG. 19, $S_3$ represents a spectrum of the reset pulse $\phi_R$. Due to the phase modulation, there is produced a side band $S_4$. Since the output signal of the demodulator 125 is supplied to BPF 126, the side band $S_4$ is reproduced as the sinusoidal signal.

The timing pulse generator 129 for generating the sampling pulses SHP-1, SHP-2 and synchronous detection signal for the synchronous detector 132 is driven by the clock pulse generated from the clock pulse generator 133. The output signal of the generator 133 is also supplied to a frequency divider 134 whose frequency division rate is same as that of the frequency divider 120, i.e. ¼. The oscillation frequency of the generator 133 is same as that of the VCO 119 and is equal to 14 MHz. Therefore, the output frequency of the frequency divider 134 is equal to 14/4 MHz. The timing pulse generator 129 further generates the horizontal synchronizing signal HD. This horizontal synchronizing signal HD is the same as the horizontal transfer signal $\phi_R$ generated from the driving signal generator 115 and is used to reset the frequency divider 134. The output signal of the frequency divider 134 is supplied to the other input of the phase comparator 127. The phase comparator 127 is formed by a sample and hold circuit to sample and hold the sinusoidal output signal from BPF 126 at the timing of the output signal of the frequency divider 134. In this manner, at the output of the phase comparator 127 there is produced DC voltage having an amplitude which is proportional to a phase difference between the output of the frequency divider 134 and the output of BPF 126. As explained above the output signal of the frequency divider 134 is equal to the output signal of the oscillator 133 divided by 4. The output signal of BPF 126 is obtained by demodulating the output signal of VCO 119 divided by 4, so that the DC voltage generated from the phase comparator 127 represents the phase difference between the output signal of the VCO 119 and that of the oscillator 133. This output signal of the phase comparator 127 is applied to a positive input of a differential amplifier 135, to a negative input of which is applied a reference voltage produced by a reference voltage source 136. The reference voltage is set to be equal to an output voltage of the phase comparator when the output signal of the frequency divider 134 and the output signal of BPF 126 have the predetermined optimum phase relationship. By controlling the oscillation frequency of VCO 119 in accordance with the output signal of the differential amplifier 135, the oscillation frequency and phase of the VCO 119 are automatically made identical with those of the oscillator 133. In this manner, the so called AFC circuit is constructed, and the phase of the reset pulse contained in the output signal of CCD 113 and received by the video processor unit 114 becomes completely and automatically coincided with the output signal of the oscillator 133 which serves as the clock pulse source for the timing pulse generator 129. The sampling pulses SHP-1 and SHP-2 for the double sampling circuit 128 are obtained by counting down the output pulse of the oscillator 133, so that the relative phase of the sampling pulses SHP-1 and SHP-2 and the output signal of CCD 113 become coincident with each other as shown in FIG. 2 regardless of the cable length.

FIG. 20A shows the carrier wave appearing at the output of BPF 131 and this carrier wave is amplitude-modulated in accordance with the chrominance signal, in the present embodiment the color difference signal. FIG. 20B shows the synchronous detection pulse generated from the timing pulse generator 129. In order to reproduce the color signal faithfully the mutual phase of the carrier and the synchronous detection pulse has to be completely identical with each other. In the present embodiment, the synchronous detection pulse is set to the peak position of the sinusoidal carrier. In the output signal of CCD 113, the color difference signals R-Y and E-Y appear with being imposed on the carrier, so that if the timing of the sychronous detection deviates, the color difference signals might interfere with each other to produce a color mixture. According to the invention by constructing the AFC circuit as explained above, the phase of the output signal of CCD 113 received at the video processor unit 114 becomes constant regardless of the cable length, so that it is possible to effect the sychronouse detection always correctly even if the cable length differs from the standard value.

It should be noted that in the present embodiment the sample and hold means is formed by the synchronous detector 130, but it may be composed of a multiplier.

Further in the present embodiment, the frequency dividers 120 and 134 are reset by the horizontal synchronizing signal HD. Although not shown FIG. 15, in order to drive the CCD 113, it is necessary to transmit the vertical transfer pulse having a period of HD i.e., 15.75 KHz in the NTSC system. The timing pulse generator 129 generates a clamper pulse for clamping the optical black and synchronizing signals which are required in the succeeding processing circuits and these signals have also a period of HD. If the mutual phase relationship of these signals having HD period is not maintained correctly, the center position viewed in the horizontal direction might be deviated as shown an arrow A in FIG. 17C. This problem can be solved by resetting the counting operation of the timing pulse generator 129 by the signal HD generated from the driving signal generator 115 so that these signals have the same phase. Due to the same reason, by resetting the counting operation of the timing pulse generator 129 by the vertical synchronizing signal VD generated from the driving signal generator 115, the center of the view angle is prevented from being shifted in the vertical direction as shown by an arrow B in FIG. 17C.

FIG. 21 is a block diagram illustrating another embodiment of the video camera apparatus according to the invention. In the present embodiment, portions similar to those shown in the previous embodiment are denoted by same reference numerals. In the previous embodiments, the reset pulse $\phi_R$ generated from the driving signal generator is phase-modulated, but according to the invention it is also possible to frequency-modulate the reset pulse $\phi_R$. In the present embodiment there is provided a mixer 141 between differential amplifier 135 and a VCO 119 and the output signal of the gate circuit 121 is added to the output signal of the differential amplifier 135. Therefore, VCO 119 is frequency-modulated in accordance with the signal supplied from the gate circuit 121 and having the frequency of 14/4 MHz, and thus the clock signal is frequency-modulated, so that the reset pulse $\phi_R$ is also frequency-modulated at the frequency of 14/4 MHz. Since the demodulator can demodulate both the phase-modulated signal and frequency-modulated signal, the circuit construction of the demodulator is the same as that of the previous embodiment so that its detailed explanation is omitted.

Figure 22:
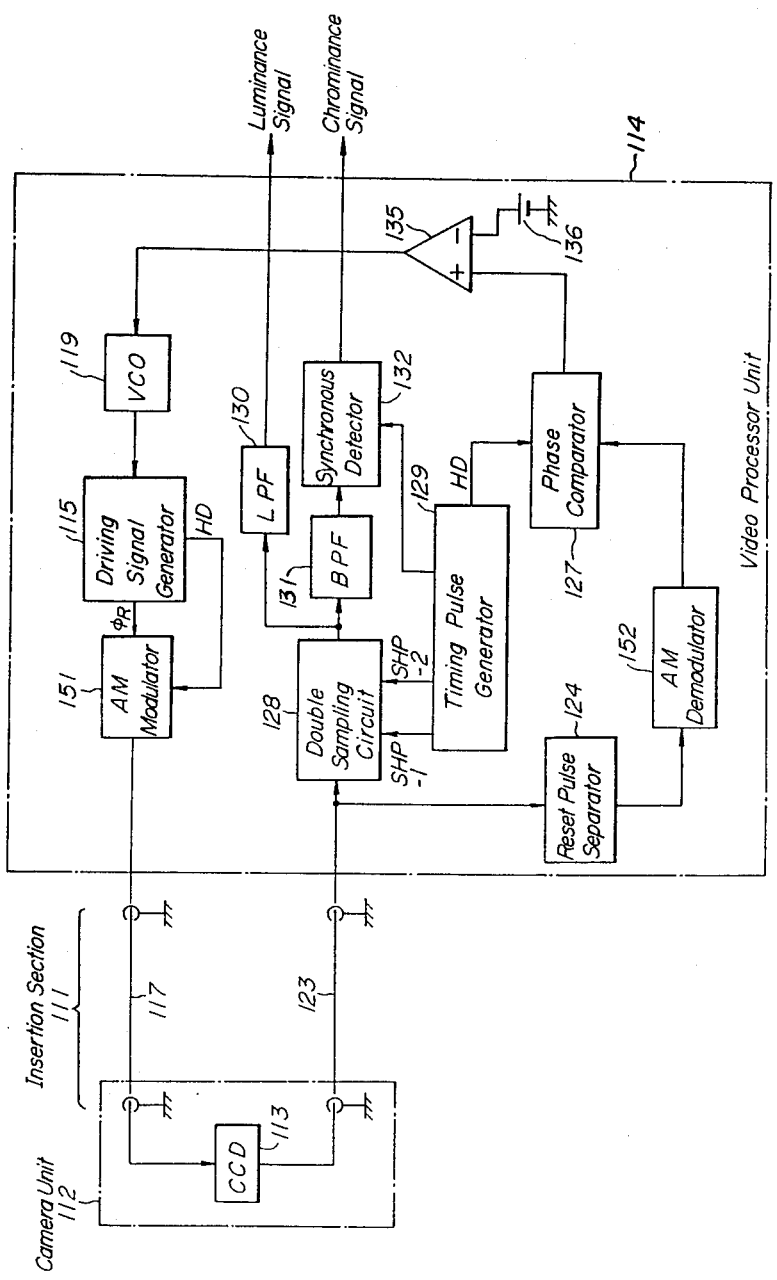
FIG. 22 is a block diagram illustrating another embodiment of the video endoscope apparatus according to the invention.

FIG. 22 is a block diagram showing still another embodiment of the video endoscope apparatus according to the invention. In the present embodiment, portions similar to those shown in FIG. 15 are denoted by the same reference numerals used in FIG. 15. In this embodiment, after the reset pulse $\phi_R$ generated from the driving signal generator 115 is amplitude-modulated by an amplitude-modulator 151, the amplitude-modulated signal is supplied to CCD 113 through a signal line 117. To the amplitude-modulator 151 is supplied the horizontal synchronizing signal HD generated from the driving signal generator 115 as the modulation signal. FIG. 23A shows the reset pulse $\phi_R$ modulated in accordance signal HD and FIG. 23B illustrates the modulation signal HD. In the present embodiment, since the modulation of 100% is effected, the reset pulse $\phi_R$ is completely removed during the period of the signal HD. The output signal from the CCD 113 is transmitted through a signal line 123 to a video processor unit 114 and is supplied to a double sampling circuit 128 and a reset pulse separator 124. The double sampling circuit 128 produces the output signal in which 1/f noise and preset pulse component have been removed. This output signal from the double sampling circuit 128 is supplied to LPF 130 to derive a luminance signal, and at the same time is supplied to BPF 131 to derive or separate a color subcarrier which is then supplied to a synchronous detector 132. In the synchronous detector 132 the color difference signals are separated. The reset pulse separated by the reset pulse separator 124 is supplied to an AM demodulator 152 to demodulate the horizontal synchronizing signal HD which corresponds to the output signal of the driving signal generation 115. The sampling pulse generation 129 supplies the sampling pulses to the double sampling circuit 128 and also supplies the synchronous detection pulse to the synchronous detector circuit 132. The sampling pulse generator 129 further generates the horizontal synchronizing signal HD synchronized with the synchronous detection pulse. The demodulated synchronizing signal HD generated from the AM demodulator 152 and the output signal HD from the sampling pulse generator 129 are supplied to a phase comparator 127 to derive a D.C. voltage in proportion to the phase difference therebetween. In a differential amplifier 135, this D.C. voltage is compared with the reference voltage given by a reference voltage source 136 to derive a difference therebetween. This difference is supplied to a VCO 119 to control its oscillation frequency. In this manner there is provided the AFC loop and the phase of the synchronizing signal HD generated from the timing pulse generator 129 becomes identical with the phase of the demodulated synchronizing signal HD. It should be noted that the reference voltage of the reference voltage source 136 is determined to be equal to the D.C. voltage from the phase comparator 127 when the two synchronizing pulses HD are synchronized with each other optimally. In this manner, the phase of the reset and $\phi_R$ is synchronized with the output pulses Of the timing pulse generator 129, and the sampling pulses for the double sampling circuit 128 are automatically brought coincident with the synchronous detection pulse regardless of the cable length.

Figure 24:
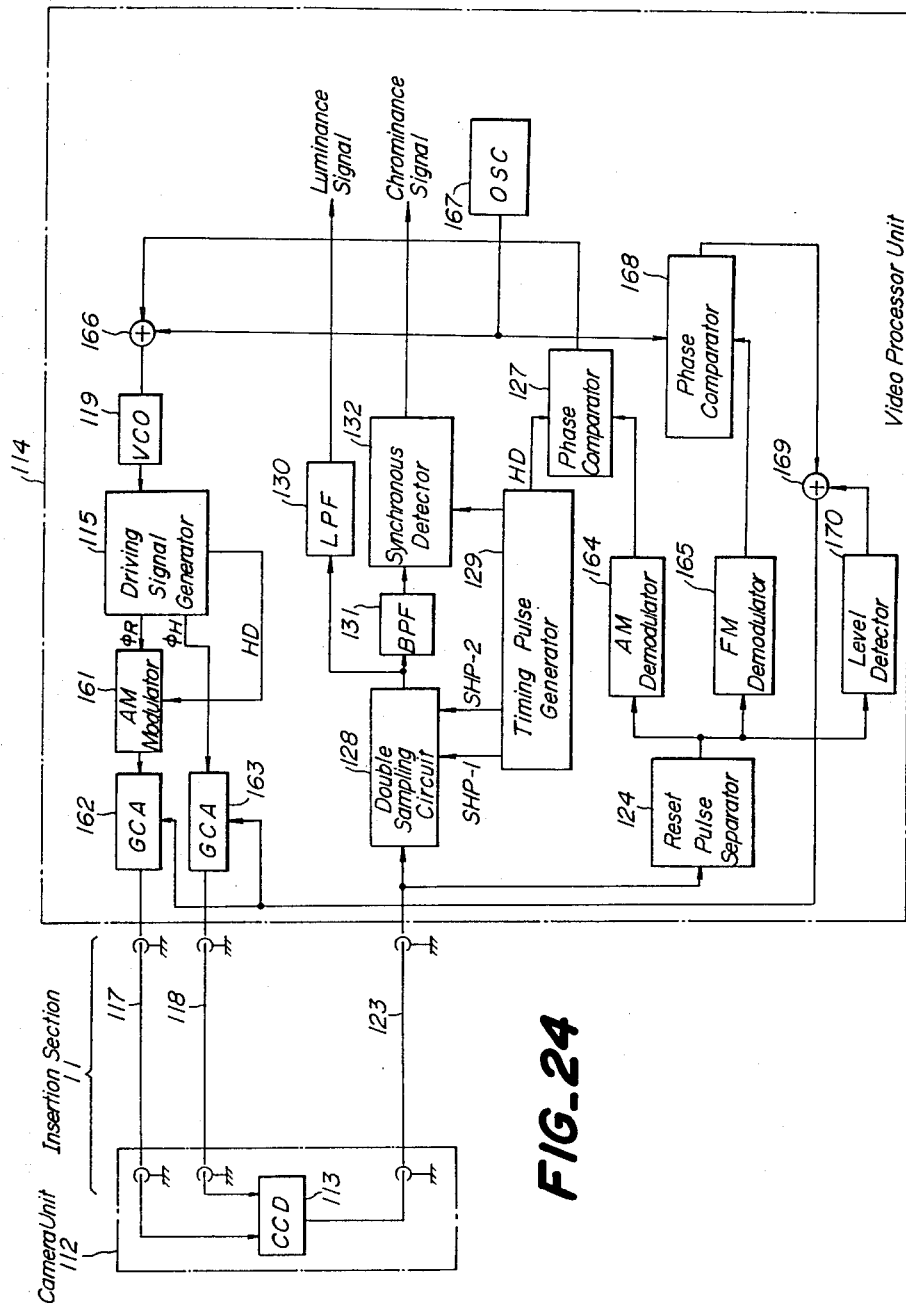
FIG. 24 is a block diagram depicting another embodiment of the video endoscope apparatus according to the invention.

FIG. 24 is a block diagram depicting another embodiment of the video endoscope apparatus according to the invention. The construction of a camera unit 112 provided in a distal end of an insertion section 111 is the same as that of the known video endoscope and comprises a solid state image sensor 113 formed by CCD. In the present embodiment, a mosaic color filter is arranged on a front surface of the CCD 113, and thus the apparatus operates as a simultaneous television system. A video processor unit 114 comprises a driving signal generator 115 to generate reset pulse $\phi_R$ and horizontal transfer pulse $\phi_H$. The reset pulse $\phi_R$ is modulated by an amplitude-phase modulator 116 and then is supplied to the CCD 113 through a gain control amplifier (GCA) 162 and a cable 117. When the reset pulse $\phi_R$ is amplitude-modulated, the reset pulse portion contained in an output signal from the CCD 113 is correspondingly amplitude-modulated.

The video processor unit 114 further comprises a voltage controlled oscillator (VCO) 119 for generating a clock pulse for the driving signal generator 115. In the present embodiment, the output frequency of the VCO 119 is set to 14 MHz. Repetion frequencies of the reset pulse $\phi_R$ and horizontal transfer pulse $\phi_H$ are set to 7 MHz. The horizontal synchronizing signal HD generated from the driving signal generator 115 is supplied to the amplitude-modulator 116 as a modulation signal. The horizontal transfer signal $\phi_H$ supplied from the driving signal generator 115 is supplied to the CCD 113 via a GCA 163 and a signal cable 118.

The output signal from the CCD 113 is supplied to a double sampling circuit 128 and is double-sampled by means of sampling pulses SHP-1 and SHP-2 supplied from a timing pulse generator 129, so that 1/f noise is mainly removed. The output signal of the double sampling circuit 128 is further supplied to a low pass filter (LPF) 130 to derive a luminance signal. The output signal is further supplied to a band pass filter (BPF) 131 and is then supplied to a synchronous detector 132 to derive a chrominance signal.

The output signal from the CCD 113 is also supplied to a reset pulse separator 124 to extract the reset pulse contained therein. The reset pulse thus extracted is supplied to an amplitude-demodulator 164 and a frequency-demodulator 165 to demodulate the amplitude-modulated component and the frequency-modulated component. In the amplitude modulator 161, the reset pulse $\phi_R$ is used as a carrier and the horizontal synchronizing signal HD is used as the modulation signal, so that the amplitude-demodulator 164 demodulates the horizontal synchronizing signal. The thus demodulated signal is supplied to one input of a phase comparator 127, to the other input of which is supplied the original horizontal synchronizing signal HD generated by the timing pulse generator 129 to derive a D.C. voltage in proportion to the phase difference therebetween. This D.C. voltage is applied via a mixer 166 to the VCO 119. By controlling the oscillation frequency of VCO 119 in accordance with the output signal of the phase comparator 127, the frequency and phase of the output signal of VCO 119 are automatically brought coincident with those of the timing pulse generator 129. In this manner, there is formed the AFC circuit which ensures that the phase of the reset pulse contained in the output signal from the CCD 113 and received at the video processor unit 114 is automatically phase-locked with respect to the sampling pulses SHP-1, SHP-2 supplied from the timing pulse generator 129.

To the mixer 166 is also supplied the output signal from an oscillator 167, so that the VCO 119 is frequency-modulated with the output signal from the oscillator 167. In the present embodiment, the oscillation frequency of this oscillator 167 is set to 1 MHz. The frequency-demodulator 165 demodulates this frequency modulation signal whose phase is compared with the output signal from the oscillator 167 in a phase comparator 168. The output signal from this phase comparator 168 then represents the length of the cable. The output signal from the phase comparator 168 is supplied via a mixer 16 to GCAs 167 and 163 as the gain control signal to control the level of driving signals $\phi_R$ and $\phi_H$ to be supplied to CCD 113.

The reset pulse Separated by the reset pulse separator 124 is also supplied to a level detector 170 to detect a magnitude of the reset pulse which is converted into a D.C. voltage. The magnitude of the reset pulse is changed in accordance with the cable length, so that the output D.C. voltage of the level detector 170 represents the length of the cable. This D.C. voltage is applied to the mixer 169 and the gain of the GCAs 162, 163 is controlled. In this case, when the output signal of the frequency-demodulator 165 lags with respect to the output signal of the oscillator 167, the output signal of the phase comparator 168 serves to increase the level of the driving signals $\phi_R$, $\phi_H$, and When the level of the reset pulse is decreased, the output signal of the level detector 170 serves to increase the level of the driving signal $\phi_R$, $\phi_H$. In the present embodiment, the output signals from the phase comparator 168 and level detector 170 are combined in the mixer 169 and the GCAs 162, 163 are controlled by the combined signal, but the GCAs may be controlled by one of these output signals.

Figure 25:
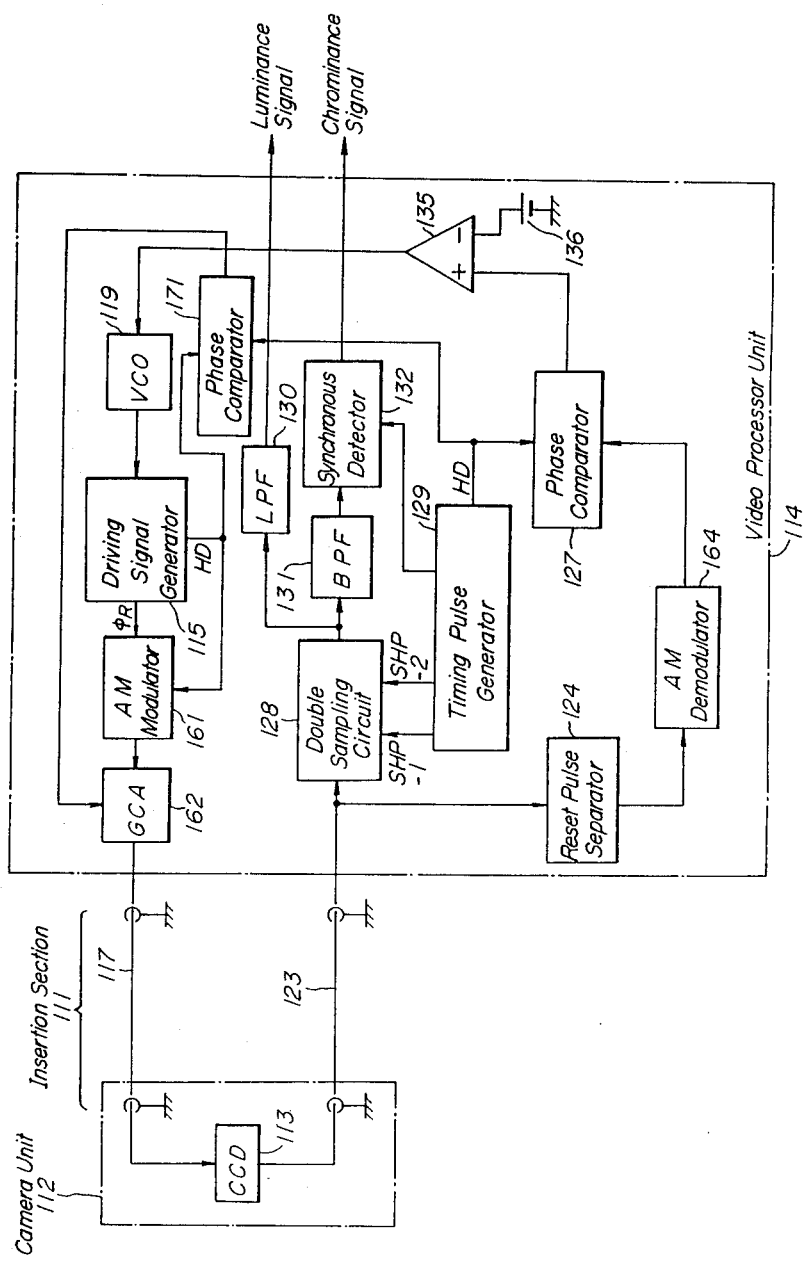
FIG. 25 is a block diagram illustrating still another embodiment of the video endoscope apparatus according to the invention.

FIG. 25 is a block diagram illustrating a modification of the embodiment shown in FIG. 24, so that portions similar to those of the previous embodiment are denoted by the same reference numerals as those used in FIG. 24. In the present embodiment, the reset pulse $\phi_R$ generated from a driving signal generator 115 is amplitude-modulated by an amplitude-modulator 161 and then is supplied to a CCD 113 via a gain controller 162 and a cable 117. To the amplitude modulator 161 is supplied the horizontal synchronizing signal HD from the driving signal generator 115 as the modulation signal. FIG. 26A shows the reset pulse $\phi_R$ modulated by the signal HD, and FIG. 26B illustrates the signal HD. In the present embodiment, during the period of the signal HD, the reset pulse $\phi_R$ is completely removed, because the modulation of 100% is carried out. The output signal from the CCD 113 is supplied via a cable 123 to a double sampling circuit 128 and a reset pulse separator 124. The double sampling circuit 128 generates the image signal having 1/f noise and reset pulse components removed therefrom. From the output signal of the double sampling circuit 128 is derived the luminance signal by means of LPF 130, and at the same time, the chrominance signal is extracted with the aid of a BPF 131, the chrominance signal being further supplied to a synchronous detector 132. The synchronous detector 132 detects the color difference signals which are further supplied to succeeding circuits. The reset pulse extracted by the reset pulse separator 124 is supplied to an amplitude-demodulator 164 and the horizontal synchronizing signal HD is demodulated. The thus demodulated signal is supplied to one input of a phase comparator 127, to the other input of which is supplied the original horizontal synchronizing signal HD generated by the timing pulse generator 129 to derive a D.C. voltage in proportion to the phase difference therebetween. This D.C. voltage is compared with a reference voltage given by a reference voltage source 136 in a differential amplifier 165 to derive a difference therebetween, the difference being supplied to the VCO 119. By controlling the oscillation frequency of VCO 119 in accordance with the output signal of the differential amplifier 165, the phase of the output signal of VCO 119 is automatically brought coincident with that of the horizontal synchronizing signal HD from the timing pulse generator 129. In this manner, there is formed the AFC circuit for keeping the phase of the reset pulse contained in the output signal from the CCD 113 and received at the video processor unit 114 coincident with the output signal HD from the timing pulse generator 129. It should be noted that the reference voltage is set to such a value that it becomes equal to the D.C. voltage which is generated from the phase comparator 127 when the two signals HD are phase-locked optimally.

In the manner explained above, the reset pulse $\phi_R$ and the output pulse from the timing pulse generator 129 are phase-locked With each other, and the Sampling pulses for the double sampling circuit 128 and the synchronous detection pulse for the sychronous detector 132 are brought into the optimal phase relationship regardless of the cable length.

Further, a phase difference between the signal Hd from the driving signal generator 115 and the signal HD from the timing pulse generator 129 is derived by a phase comparator 171 to produce a D.C. voltage in proportion to the cable length. This D.C. voltage is used to control the GCA 162. In this manner, the level of the driving signal for the CCD 113 can be adjusted to the desired value regardless of the cable length.

In the above embodiments, the driving signal for the CCD 113 is modulated and the modulation component contained in the output signal from the CCD is demodulated to detect the information about the cable length. According to the present invention, it is not always necessary to effect such a demodulation. This will be further explained hereinbelow.

Figure 27:
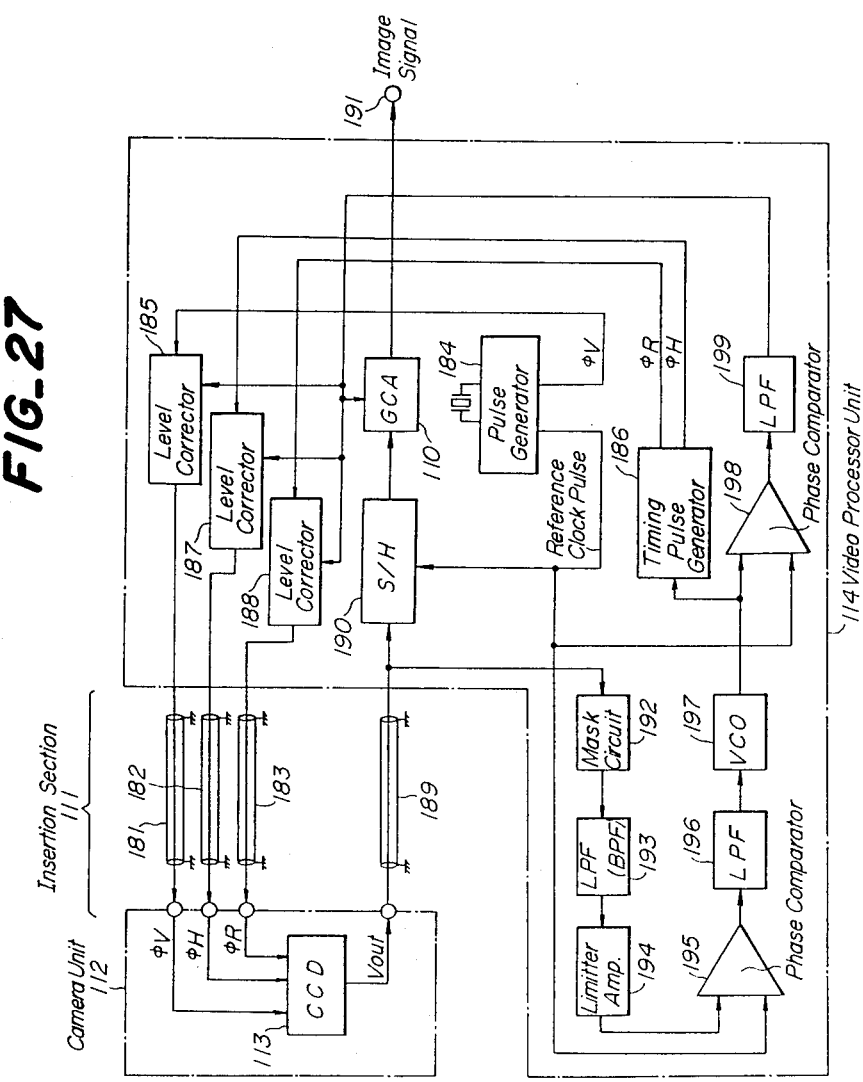
FIG. 27 is a block diagram showing another embodiment of the video endoscope apparatus according to the invention.

FIG. 27 is a block diagram illustrating still another embodiment of the video endoscope apparatus according to the invention. In the present embodiment, vertical transfer pulse $\phi_V$, horizontal transfer pulse $\phi_H$ and reset pulse $\phi_R$ are supplied via signal lines 181, 182 and 183, respectively to a CCD 113 provided in a camera unit 112 arranged in a distal end of an insertion section 111. A video processor unit 114 comprises a pulse generator 184 and the vertical transfer pulse $\phi_V$ generated from the pulse generator is supplied to the signal line 181 by means of a level corrector 185. The video processor unit 114 further comprises a timing pulse generator 186 for generating the horizontal transfer pulse $\phi_H$ and reset pulse $\phi_R$ which are supplied to the signal lines 182 and 183, respectively via level correctors 187 and 188, respectively. The output signal $V_{out}$ from the CCD 113 is supplied via a signal line 189 to the video processor unit 114. In the video processor unit 114, the output signal $V_{out}$ is sampled and held by a sample and hold circuit 190 under the control of a sampling pulse which is formed by a reference clock pulse generated from the pulse generator 184. The output signal of the sample and hold circuit 190 is supplied to an output terminal 191 by means a gain control amplifier (GCA) 110 as the output image signal.

The video processor unit 114 further comprises a mask circuit 192 which extracts a signal during the non-pictorial period from the output signal $V_{out}$ of the CCD 113. In the video endoseope system, as illustrated in FIG. 28, there is provided on the monitor screen an area for displaying index and this index area requires the non-pictorial period in the image signal. The mask circuit 192 operates to extract the signal within this non-pictorial period. It should be noted that the television signal includes the blanking period which is not displayed on the screen, and this blanking period may be utilized as the non-pictorial period. The non-pictorial period signal extracted by the mask circuit 192 includes the reset pulse portion $\phi_R$, and the horizontal transfer pulse $\phi_H$ may be or may not be included. In this case, it is advantageous to operate always a horizontal shift register of CCD 113 rather than to stop the operation of CCD for the non-pictorial period, because possible dark currents in the horizontal shift register could be thrown away and the S/N ratio becomes better.

The signal extracted by the mask circuit 192 is supplied to a low pass filter (LPF) 193 to derive the reset pulse portion contained in the output signal of the CCD 113. The reset pulse portion thus extracted is passed through a limiter amplifier 194 to effect the waveform shaping. In the usual CCD driving method, the reset pulse $\phi_R$ has a duty cycle of 25%, but if the duty cycle of the reset pulse is changed to 50% during the non-pictorial period, it is advantageous to use a band pass filter (BPF) instead of the low pass filter. Then lower frequency noise than the fundamental frequency can be removed, and jitter and fluctuation can be improved.

The reset pulse portion from the limiter amplifier 194 is supplied to one input of a phase comparator 195, to the other input of which is supplied the reference clock pulse generated from the pulse generator 184. Then the phase comparator 195 produces an output signal representing a phase difference between these pulses. This phase difference signal is a measure of the length of the cable lines 181~183, 189. The output signal from the phase comparator 195 is supplied to a low pass filter 196 to derive a D.C. component thereof which is then applied to a VCO 197 as a control signal. An output signal of the VCO 197 is supplied to the timing pulse generator 186 to control the phases of the horizontal transfer pulse $\phi_H$ and reset pulse $\phi_R$. In this manner, there is constituted a feedback loop including the CCD 113 as illustrated in FIG. 29. In this feedback loop, the signal line from VCO 197 to CCD 113 and the signal line from CCD 113 to phase comparator 195 produce the delay for the transmitted signals. Therefore, the feedback loop operates as a phase locked loop in which the two signals supplied to the phase comparator 195 have the identical frequency and phase. That is to say, the driving signal for the CCD 113 generated at the video processor unit has the advanced phase corresponding to the time delay due to the signal transmission cable lines. It should be noted that instead of the phase locked loop, use may be made of a phase adjusting circuit including a variable delay element.

As shown in FIG. 27 the output signal of the VCO 197 is supplied also to one input of a phase comparator 198 to the other input of which is supplied the reference clock pulse from the pulse generator 184 to derive a signal representing a phase difference between these signals. The output signal of the phase comparator 198 is supplied to a low pass filter 199 to derive a D.C. voltage representing the cable length. This D.C. voltage is applied to the level correctors 185, 187 and 188 as the level control signal. Further, the image signal derived from the sample and hold circuit 190 is supplied to the gain control amplifier 110 to which is also applied the D.C. voltage from the low pass filter 199 as the gain control signal such that the gain of the image signal is maintained constant regardless of the cable length.

Figure 30:
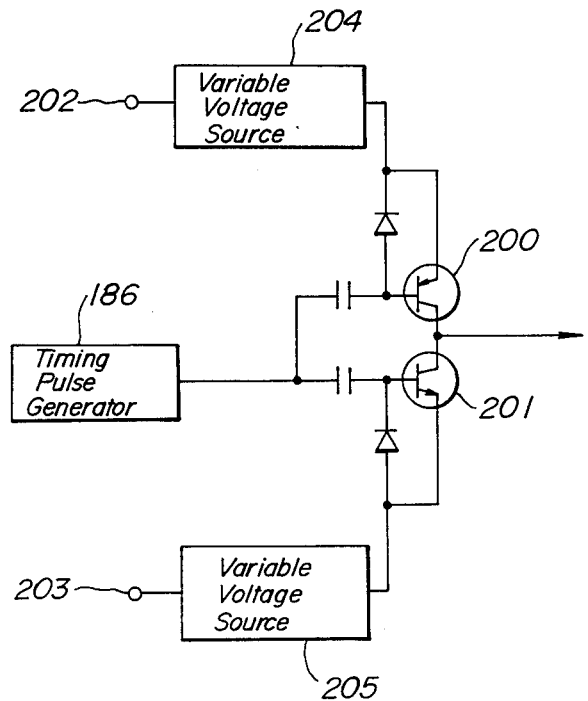
FIG. 30 is a circuit diagram illustrating the level compensator of the apparatus of FIG. 27.

FIG. 30 is a circuit diagram illustrating an embodiment of the level corrector 188 for adjusting the level of the reset pulse $\phi_R$ to be supplied to the CCD. In the present embodiment, both the upper voltage $\phi_{RH}$ and lower voltage $\phi_{RL}$ shown in FIG. 5 are adjusted. To this end, the output signal from the timing pulse generator 186 is supplied to a current buffer consisting of push-pull arrangement of transistors 200 and 201 to produce the reset pulse $\phi_R$. The output D.C. voltage produced by the low pass filter 199 is applied through control input terminals 202 and 203 to variable voltage sources 204 and 205 which determine the upper and lower limit voltages of the reset pulse $\phi_R$, respectively.

Figure 31:
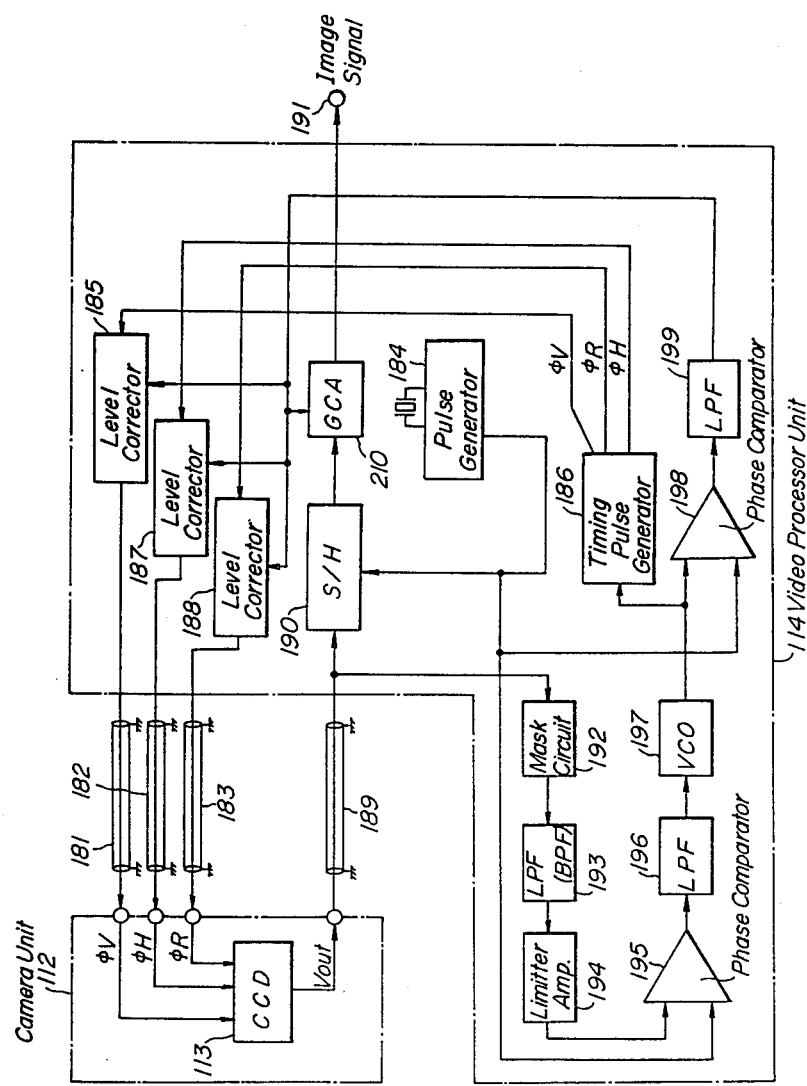
FIG. 31 is a block diagram showing a modification of the apparatus shown in FIG. 27.

FIG. 31 is a block diagram depicting another embodiment of the video camera apparatus according to the invention. In the present embodiment, portions similar to those of the embodiment illustrated in FIG. 27 are denoted by the same reference numerals used in FIG. 27. In the embodiment of FIG. 27, in order to make the phase of the output signal from the CCD 113 coincident with the phase of the sampling pulse at the sample and hold circuit 190, the phase of the driving signal $\phi_R$, $\phi_H$ for the CCD 113 produced by the timing pulse generator 186 is controlled. In the present embodiment, the phase of the sampling pulse for the sample and hold circuit 190 is controlled. To this end, the reset pulse portion which is extracted and waveform-shaped by means of the mask circuit 192, low pass filter 193 and limiter amplifier 194 is converted into continuous clock pulses having the same phase by a phase locked oscillator composed of the phase comparator 195, low pass filter 196 and VCO 197. The continuous clock pulses are supplied to the sample and hold circuit 190 as the sampling pulses.

The continuous clock pulse is supplied to the phase comparator 198 together with the reference clock pulse generated from the pulse generator 184 to derive a pulse difference between these clock pulses, said phase difference representing the time delay due to the signal cable. The output signal from the phase comparator 198 is supplied to the low pass filter 199 to derive a D.C. voltage which is then applied to level correctors 185,187 and 188 as the level control signal so that the level of the driving signal for the CCD is corrected, and at the same time, the D.C. voltage is applied to a gain control amplifier 210 to adjust the gain of the image signal in accordance with the cable length.

Figure 32:
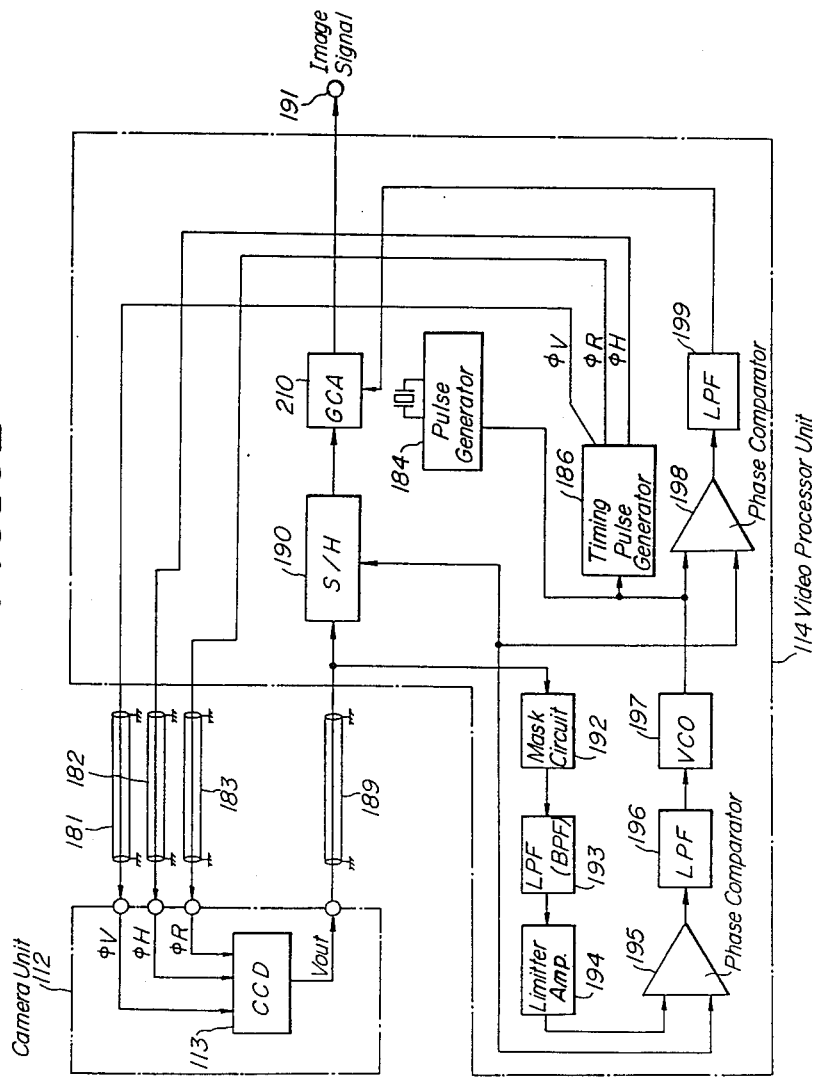
FIG. 32 is a block diagram showing a modification of the embodiment illustrated in FIG. 27.

FIG. 32 is a block diagram showing a modification of the embodiment shown in FIG. 31 of the video camera apparatus according to the invention, and the portions similar to those of the previous embodiment are denoted by the same reference numerals used in FIG. 31. In the embodiment of FIG. 31, the D.C. voltage representing the cable length is detected by the low pass filter 199 and is supplied to the level correctors 185, 187, 188 as the level control signal for adjusting the level of the driving signal to, be supplied to the CCD as well as to the gain control amplifier 210 for adjusting the level of the output image signal from the sample and hold circuit 190. In the present embodiment, the level correctors are omitted and the D.C. control voltage from the low pass filter 199 is applied only to the gain control amplifier 210 to control the amplitude of the image signal in accordance with the cable length. The remaining construction of the present embodiment is entirely the same as the previous embodiment, so that its explanation is omitted.

Figure 33:
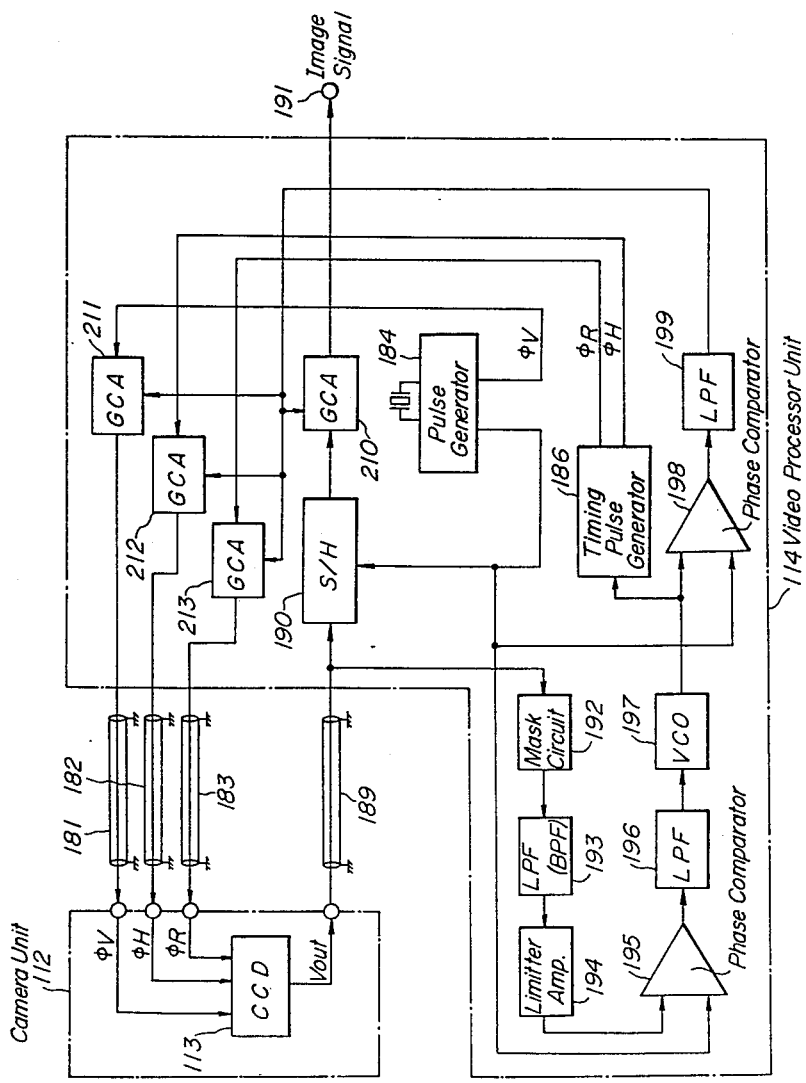
FIG. 33 is a block diagram depicting another modification of the apparatus of FIG. 27.

FIG. 33 is a block diagram showing still another embodiment of the video camera apparatus according to the invention. In the present embodiment, instead of the level correctors 185, 187 and 188 there are provided gain control amplifiers (GCA) 211, 212 and 213 which adjust not only the level of the driving signal but also the frequency characteristic so that the decay of the high frequency components due to the signal cable can be compensated for. To this end, the D.C. voltage obtained by the low pass filter 199 and representing the cable length is applied to the GCAs 211, 212 and 213 so that the peak values and frequency characteristics of the driving pulses $\phi_R$, $\phi_H$ and $\phi_V$ to be supplied to the CCD 113 are adjusted in accordance with the length of the signal cable. The GCAs 211, 212 and 213 has the frequency characteristic shown in FIG. 34, in which the gain of the signal is made larger in accordance with the increase of the D.C. voltage and the peaking is effected for the high frequency components. The amplifiers have equalizers having such characteristics. Further, a gain control amplifier 210 for amplifying the image signal from the sample and hold circuit 190 has a frequency characteristic illustrated in FIG. 35. This frequency characteristic also has the peaking function in the high frequency range.

FIG. 36 is a circuit diagram showing another embodiment of the gain control amplifiers 210–213. In the present embodiment, there are provided gain control circuits 215 and 216 having a flat frequency characteristic, and the input signal is supplied to the gain control circuit 215 directly and to the gain control circuit 216 via a differentiating circuit 219 composed of a capacitor 217 and a resistor 218. The output signals from the gain control circuits 215 and 216 are added to each other in an adder 220 to produce a gain controlled output signal.

In this manner, the high frequency component in the image signal is extracted by the differentiating circuit 219 and after adjusting the gain of the extracted high frequency component by the gain control circuit 216, the high frequency component having the adjusted gain is added to the output signal from the gain control circuit 215, so that both the decay of the level and the decay of the high frequency component can be optimally compensated for.

FIG. 37 is a block diagram showing another embodiment of the video endoscope apparatus according to the invention. In the present embodiment, a video processor unit 304 comprises a differential amplifier 312 for comparing the output image signal supplied from a double sampling circuit 308 with a reference voltage given by a reference voltage source 211, and a variable delay line 313 whose delay time is controlled by the output signal from the differential amplifier 312. The driving signal produced by a driving signal generator 307 is supplied by means of the variable delay line 313 to a solid state image sensor 302, e.g. CCD provided in a camera unit 303 via a first signal line 305 of a signal cable. The CCD 302 is arranged in a distal end of an insertion section 301.

Figure 38:
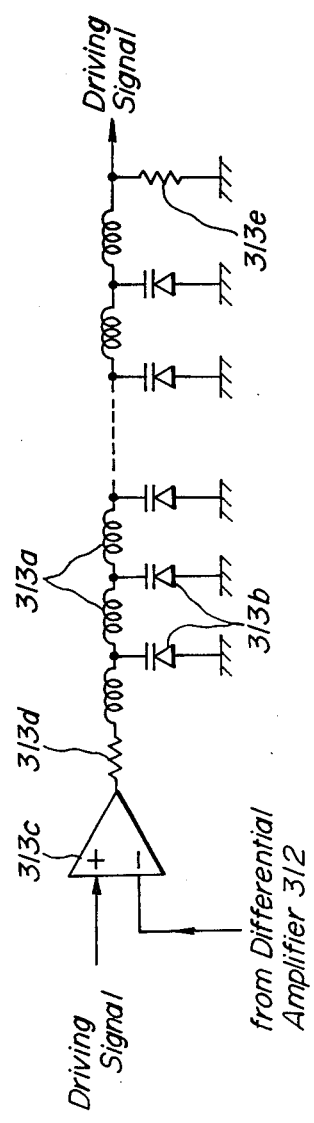
FIG. 38 is a circuit diagram illustrating the variable delay line of the apparatus shown in FIG. 37.

FIG. 38 is a circuit diagram illustrating a detailed construction of the variable delay line 313. The variable delay line 313 comprises inductors 313a, variable capacitance diodes 313b, a differential amplifier 313c, a matching resistor 313d and an output resistor 313e. The variable capacitance diode is called VARICAP and its capacitance is changed in accordance with an applied voltage. To a positive input of the differential amplifier 313c is supplied the driving signal for the CCD generated from the driving signal generator 307, and to a negative input is applied the output voltage of the differential amplifier 312. A difference voltage derived from the differential amplifier 313c is applied to the delay line of distributed constant type composed of the inductors 313a and variable capacitance diodes 313b. The capacitance values of the variable capacitance diodes 313b are changed in accordance with the D.C. bias voltage of the output signal from the differential amplifier 313c which corresponds to the output voltage of the differential amplifier 312. Therefore, the delay time of the variable delay line 313 is changed in accordance with the output voltage of the differential amplifier 312.

In FIG. 37, the output image signal of the double sampling circuit 308 is compared with the reference voltage in the differential amplifier 311. This reference voltage is so set that it is equal to the image signal which is obtained when the sampling is effected at the correct phase position for an endoscope having a predetermined standard cable length. Therefore, when use is made of an endoscope having the cable length different from said standard cable length and the sampling phase is deviated, the output voltage from the differential amplifier 312 becomes larger and thus the output voltage from the differential amplifier 313c in the variable delay line 313 becomes lower. Therefore, the delay time of the variable delay line 313 becomes shorter and the image signal from the CCD 302 becomes close to the waveform shown by the solid line in FIG. 4A. In this manner, the negative feedback loop is constituted and the output signal of the CCD 302 is automatically adjusted to have the correct phase relationship with respect to the sampling signals SHP 1 and SHP-2.

FIG. 39 is a block diagram showing still another embodiment of the video processor unit of the video camera apparatus according to the invention. As explained above, the reset pulse in the CCD driving signal is superposed on the output signal from the CCD as shown in FIG. 2A. In the present embodiment, the video processor unit comprises a reset pulse separator 331 for separating and extracting the reset pulse portion $S_A$ in the output Signal supplied from the CCD via the signal cable, and a sawtooth signal generator 332 which is triggered by an output pulse of the reset pulse separator 331. A sawtooth signal generated from the generator 332 is supplied to one input of a phase comparator 333. A driving signal generated from a driving signal generator 307 is supplied via a signal cable 305 to the CCD. This driving signal is also supplied to the other input of the phase comparator 333 via a phase shifter 334.

Now the operation of the video processor unit will be explained also with reference to signal waveforms shown in FIGS. 40A~40D. FIG. 40A illustrates the output signal of the CCD, FIG. 40B the output signal of the reset pulse separator 331, and FIG. 40C depicts the sawtooth signal from the sawtooth signal generator 332. The phase comparator 333 is formed by a sample and hold circuit and samples the sawtooth signal with the reset pulse which has been phase-shifted by the phase shifter as shown in FIG. 40D and holds the thus sampled value. Therefore, the output voltage of the phase comparator 333 represents a phase difference between the reset pulse in the driving signal and the reset pulse portion $S_A$ in the output Signal of the CCD, and this phase difference is a measure of the length of the cable lines 305, 306. The output voltage of the phase comparator 333 is compared in a differential amplifier 312 with a reference voltage generated by a reference voltage source 311 to derive a difference therebetween and the delay time of a variable delay line 313 is controlled in accordance with the difference output signal of the differential amplifier 312. In this manner, the feedback loop is provided and the phase of the output signal of the CCD is automatically adjusted to have the optimum phase with respect to the sampling signals SHP-1 and SHP-2 for a double sampling circuit 308. There is further arranged a phase shifter 334 which gives phase off-set to the sampling pulse at the phase comparator 333 such that the output pulse of the phase shifter becomes coincident with a center point of the sawtooth signal when use is made of the endoscope having the standard cable length.

FIG. 41 is a block diagram illustrating still another embodiment of the video processor unit of the video camera apparatus according to the invention. The video processor unit of this embodiment is to be used for a camera unit of the simultaneous color television system in which red, green and blue mosaic color filter is arranged on a front surface of CCD. Therefore, the output signal from the double sampling circuit 308 is supplied to R/B detector 335 in which the sample and hold is carried out in accordance with a detecting clock pulse to derive a chrominance signal. In the embodiment shown in FIG. 37, the D.C. bias level in the output signal of the double sampling circuit 308 is detected and the delay time of the variable delay line 313 is adjusted in accordance with the detected D.C. level, so that it is impossible to correct an error due to a phase drift of the detecting clock pulse for the R/B detector 335. Further, in the embodiment of FIG. 37, when the relative phase of the sampling pulses SHP-1 and SHP-2 drifts and the output of the double sampling circuit 308 increases, the output of the R/B detector 335 is also increased, so that even if the R/B information is not existent, there might be erroneously produced the R/B information. In order to avoid the above problems, in the embodiment shown in FIG. 41, the output signal of the double sampling circuit 308 is supplied to the R/B detector 335 and is sampled and held by the detecting clock pulse which is synchronized with the driving signal produced by the driving signal generator 307 to detect respective color signals. The color signals thus detected are supplied to a positive input of a differential amplifier 312 via a mask circuit 336. A masking signal for the mask circuit 336 ensures passage of the signal only for the non-pictorial period during which the image is not displayed on the monitor screen.

FIGS. 42A-42C show signal waveforms for explaining the operation of the R/B detector 335. FIG. 42A illustrates schematically the output image signal from the CCD. In the present embodiment, the mosaic filter has color filter sections RGBRGB viewed in the horizontal scanning direction. FIG. 42B shows a signal for detecting the red color signal and FIG. 42C depicts a signal for selectively detecting the blue color signal. The output signal of the R/B detector 335 is compared in the differential amplifier 312 with the reference voltage and the delay time of the variable delay line 313 is controlled in accordance with the difference output signal. In this manner, it is possible to effect more precise correction than with the embodiment illustrated in FIG. 37.

FIG. 43 is a block diagram showing still another embodiment of the video processor unit according to the invention. In the embodiment of FIG. 37, since the output image signal derived from the double sampling circuit 308 is compared with the reference voltage in the differential amplifier 312, if the image signal contains a level fluctuation, the phase of the sampling pulse SHP-1 might be erroneous slightly. In practiced, since the level fluctuation of the image signal is smaller than the bias level fluctuation due to the phase drift of the sampling pulse SHP-1, the phase error of the sampling pulse due to the fluctuation of the image signal is very small. The embodiment illustrated in FIG. 43 can compensate this very small error. To this end, the output signal of the double sampling circuit 308 is supplied to a sampling circuit 341, and is sampled in a sampling unit 342 by a sampling pulse. The sampled value is then stored in a capacitor 343 and the value thus held is applied to the differential amplifier 312. The sampling pulse for the sampling unit 342 is so set that the image signal supplied from the double sampling circuit 308 can be sampled at the non-pictorial area such as the horizontal blanking area and an optical black area. Then, the phase information of the sampling pulse SHP-1 does not contain the image signal and the above mentioned error can be removed.

FIGS. 44A-44D explain how to derive the masking pulse. In the video endoscope system, since use is made of the small optical system, an image 352 is displayed on a monitor screen 351 only at its center area and the peripheral area is masked as illustrated in FIG. 44A. FIG. 44B shows the waveform of the whole image signal which includes the optical black areas 354 on both sides of the horizontal blanking area 353, and a picture signal 355 is situated between the optical black areas. The sampling pulse for the sampling circuit 341 may be set in the horizontal blanking area 353 as depicted in FIG. 44C or in the optical black area 354 as illustrated in FIG. 44D.

The present invention is not limited only to the embodiments explained above, but many modifications and alternations may be conceived by those skilled in the art within the scope of the invention. For instance, the sampling circuit 341 shown in FIG. 43 may be arranged between the phase comparator 333 and the differential amplifier 312 of the embodiment shown in FIG. 39. In this case, the slight error due to the level fluctuation of the image signal can be removed. Further the phase adjusting means may be formed by various phase changing means other than the variable delay line illustrated in FIG. 38. In the above embodiments, the camera unit is arranged in the distal end of the insertion section and is coupled with the video processor unit via the signal cable arranged within the insertion section, but the present invention is not limited to such a video endoscope apparatus and may be constructed into various kinds of video camera apparatus.

Moreover, in the above embodiments, one of the phase, frequency and peak value of the reset pulse is adjusted in accordance with the detected cable length. However, it is also possible to adjust the level of the feedthrough portion $S_B$, i.e. the D.C. level or to control a plurality of these parameters simultaneously.

In the embodiment illustrated in FIG. 32, it is not always necessary to adjust the parameters of the driving signal in an automatic manner, but one or more of these parameters may be adjusted manually in accordance with the display of the detected cable length.

In the above embodiments, the solid state image sensor is formed by the charge coupled device (CCD), but it may be constituted by any other solid state image sensors of X-Y address selection system comprising photodiodes, MOSFETs and SITs (static induction transistor).

FIG. 45 is a circuit diagram showing schematically two pixels arranged in X direction and composed of photodiodes. Cathodes of photodiodes 401 and 402 are connected in parallel with source-drain paths of X selection FETs 403, 404 and source-drain paths of Y selection FETs 405, 406, respectively. Gates of FETs 403 and 404 are connected in parallel with an X selection line 407, and gates of FETs 405, 406 are connected in parallel with a Y selection line 408. Further, source-drain paths of the FETs 405, 406 are connected in parallel with an output line 409. This output line 409 is coupled via a reset FET 410 with a reset voltage source 411 and the gate of this reset FET is connected to a reset line 412.

The reset FET 410 serves to control the accumulation time of photocarriers in the photodiodes. In the present embodiment, the reset pulse is supplied to the reset line 412 during the non-pictorial period to make on and off the reset FET 410, so that a pulse having a desired frequency is produced on the output line 409 of the solid state image sensor. This pulse is transmitted by means of the cable to the video processor unit and is processed therein in the manner explained above to derive the information about the cable length.

Figure 46:
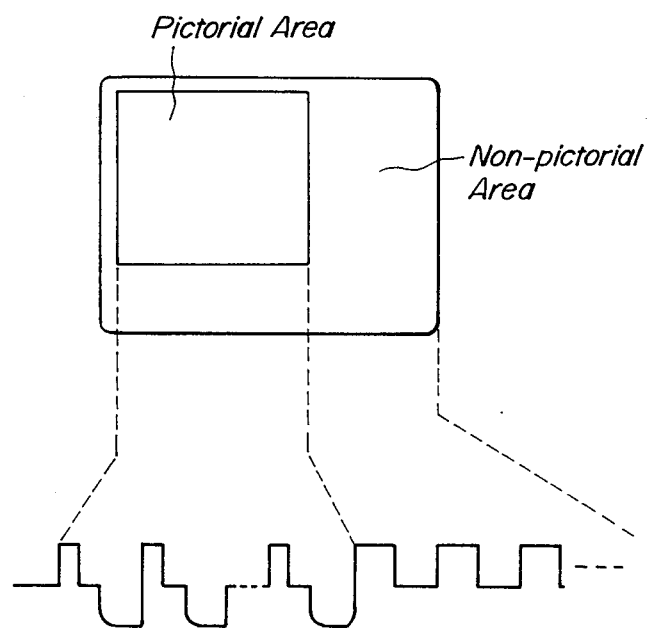
FIG. 46 is a schematic view showing the reset pulse in the pictorial and non-pictorial regions.

Since the output signal of the solid state image sensor includes the actual picture signal during the pictorial period, the duty cycle of the reset pulse $\phi_R$ could not be changed, but in the non-pictorial period, the frequency and the duty cycle of the reset pulse can be changed at will during the non-pictorial period. Therefore, the duty cycle of the reset pulse may be changed into 50% during the non-pictorial period as illustrated in FIG. 46. The increased duty cycle of the reset pulse is advantageous for removing the noise by filtering in the video processor unit. Moreover, even if the cable length is very long so that the delay time exceeds one pixel period, the delay time can be effectively detected by decreasing the reset pulse frequency within the non-pictorial period such that its period exceeds the delay time.

Further, in the above explained embodiments, the solid state image sensor is arranged in the distal end of the insertion section and the light source unit provided in the video processor unit includes the rotary filter having red, green and blue filter sections, so that the object is illuminated successively with red, green and blue illumination lights, or the mosaic color filter is arranged on the front surface of the solid state image sensor to derive the red, green and blue color signals simultaneously.

FIG. 47 is a perspective view showing various combinations of endoscopes and a main external unit. The main external unit 501 comprises a light source unit and a video processor unit for the field or frame sequential television system as well as a light source unit and a video processor unit for the simultaneous television system. On a front panel of the main external unit 501, there are provided sockets 502 and 503 for the light source unit and video processor unit for use in the sequential television system, and sockets 504 and 505 for the light source unit and video processor unit for use in the simultaneous television system. A video endoscope 506 for the sequential television system having the solid state image sensor provided in the distal end of the insertion section and a fiberscope with a sequential television system camera arranged at an eyepiece of the fiberscope are coupled with the sockets 502 and 503. A video endoscope 508 of the simultaneous television system having the solid state image sensor with the mosaic color filter arranged in the distal end of the insertion section and an optical fiberscope 509 having a solid state image sensor with the color mosaic filter arranged at an eyepiece are coupled with the sockets 504 and 505. A usual fiberscope 510 is connected to the socket 504. In this manner, a plurality of video endoscopes and the usual fiberscope can be utilized together with the single main external unit 501 to display a color image on a color monitor 511. In this case, although these video endoscopes have different cable lengths, it is possible to pick-up the image of the object under the optimum condition by detecting the cable length and adjusting the driving signal for the solid state image sensor and/or the level, amplitude and frequency characteristics of the image signal in accordance with the detected cable length.

In the embodiment illustrated in FIG. 47, the light source units and videoprocessor units are provided in the same housing, but they may be provided separately as shown in FIG. 48. In this embodiment, the light source unit is commonly used for the sequential and simultaneous television systems. In FIG. 48, a video endoscope 550 comprises a solid state image sensor having the color mosaic filter arranged thereon, so that this video endoscope apparatus works on the simultaneous television system. A connector 551 provided at the end of a light guide 559 is coupled with a socket 553 of a light source unit 552, and a connector 554 provided at the end of the cable is coupled with a socket 556 of a video processor unit 555. The light source unit 552 includes a lamp 557 for emitting white light, and a lens system 558 for focusing the light onto an incident face of the light guide 559. Into an optical path of the lens system 558 a rotary filter 560 having red, green and blue color sections is inserted, and the rotary filter is rotated by a motor 561. A rotation phase of the rotary filter is detected by a sensor 562 and an output signal of the sensor is supplied to a timing generator 563 to generate a timing pulse in synchronism with the rotation of the rotary filter. The timing pulse is then supplied to a contact 564. When use is made of the video endoscope of the sequential television system, the light source unit 552 is connected to the video processor unit of the sequential television system by means of the contact 564, but when use is made of the video endoscope of the simultaneous television system, the contact 564 is not connected anywhere. The connection condition of the contact 564 is detected by a connection detector 565 and its output is supplied to a movement controller 566. The rotary filter 560, motor 561 and sensor 562 are arranged in a housing 567 and this housing is arranged movably along guide rails 568. The movement controller 566 controls the movement of the housing 567. When use is made of the video endoscope of the simultaneous television system as shown in FIG. 48, the housing 567 is set into the position shown in FIG. 48 so that the rotary filter 560 is moved out of the optical path of the lens system 558. But when the video endoscope of the sequential television system is used, the housing 567 is moved upward in the drawing of FIG. 48 such that the rotary filter 560 is inserted into the optical path.

The video processor unit 555 comprises a video processing circuit 570 which processes the output signal from the solid state image sensor to derive brightness signal Y, and color difference signals R-Y and B-Y in accordance with the simultaneous television system, an inverse matrix circuit 571 for processing the signals Y, R-Y and B-Y to generate red, green and blue color signals, and a color encoder 572 for converting these signals into the composite color television signal of NTSC system. The video processor unit 555 further includes a driver circuit 573 for generating the driving signal for the solid state image sensor, a cable length detector 574 for processing the output signal from the CCD to detect the cable length, and a clock pulse generator 575 for generating a reference clock pulse at a timing corresponding to the detected cable length. As explained above, the cable length detection signal is also supplied to the driver circuit 573 to adjust the driving signal in accordance with the cable length.

In the video camera apparatus according to the invention, the output signal supplied from the solid state image sensor via the signal cable is processed to extract the information representing the cable length and the phase, peak value and D.C. level of the driving signal for the solid state image sensor are adjusted in accordance with the detected cable length. Therefore, the solid state image sensor can be operated optimally even if the length and property of the cables are fluctuated and the circuits show the temperature drift. Further, the output signal from the solid state image sensor can be sampled at correct timings so that the image signal can be regenerated correctly and an image of high quality can be displayed. Further, in the embodiments in which the driving signal to be supplied to the camera unit is modulated and the modulation component contained in the output signal from the solid state image sensor is demodulated to derive the phase difference therebetween which represents the cable length, the cable length can be detected accurately without being affected by noise which might be induced largely into the long cable. Further, the level of the reset pulse is greatly fluctuated by the length of the cable and the phase error might be introduced in case of extracting the reset pulse from the output signal of the image sensor, but the reset pulse is used as the carrier so that even if the level of the reset pulse is changed to a large extent, the demodulated component is not affected at all, so that the cable length can be measured precisely. Moreover, in the embodiment shown in FIG. 19, since the technique of the modulation and demodulation is not adopted, the circuit construction is very simple and cheap.

What is claimed is:

1. A video camera apparatus comprising
    a camera unit including a solid state image sensor for converting an optical image of an object into an electric signal;
    a video processor unit having a driving circuit for generating a driving signal for driving the solid state image sensor and a video processing circuit for processing the electric signal supplied from the solid state image sensor to derive an image signal;
    a signal cable connected between the camera unit and the video processor unit and having a first signal line for transmitting the driving signal from the video processor unit to the camera unit and a second signal line for transmitting the electric signal supplied from the solid state image sensor from the camera unit to the video processor unit; and
    a cable length detection circuit provided in the video processor unit for processing the electric signal transmitted from the solid state image sensor via the second signal line to derive from the electric signal cable length information representing the length of said signal cable.

2. An apparatus according to claim 1, wherein said cable length detection circuit detects a magnitude property of the electric signal supplied from the solid state image sensor via the second signal line.

3. An apparatus according to claim 2, wherein said cable length detection circuit detects an amplitude of a reset pulse portion contained in said electric signal supplied from the solid state image sensor via the second signal line.

4. An apparatus according to claim 2, wherein said cable length detection circuit detects a D.C. level of the electric signal supplied from the solid state image sensor via the second signal line.

5. An apparatus according to claim 2, wherein said cable length detection circuit detects the magnitude property of the electric signal supplied from the solid state image sensor via the second signal line during a non-pictorial period.

6. An apparatus according to claim 1, wherein said cable length detection circuit detects a phase property of the electric signal supplied from the solid state image sensor via the second signal line.

7. An apparatus according to claim 6, wherein said cable length detection circuit detects a phase difference between a reset pulse portion contained in the electric signal supplied from the solid state image sensor via the second signal line and a reset pulse contained in the driving signal to be supplied to the solid state image sensor via the first signal line.

8. An apparatus according to claim 1, wherein said video processor unit further comprises a control circuit for controlling the driving circuit in accordance with the cable length information.

9. An apparatus according to claim 8, wherein said driving circuit generates horizontal and vertical driving pulses and a reset pulse for driving the solid state image sensor, and said control circuit controls at least one of D.C. level, amplitude, phase and frequency properties of one of the horizontal and vertical driving pulses and reset pulse.

10. An apparatus according to claim 1 or 9, wherein said video processor unit further comprises a control circuit for controlling the video processing circuit in accordance with the cable length information.

11. An apparatus according to claim 10, wherein said control circuit controls a gain of the image signal in accordance with the cable length information.

12. An apparatus according to claim 10, wherein said control circuit controls timings of sampling the image signal in the video processing circuit.

13. An apparatus according to claim 9, wherein said control circuit includes a comparator circuit for comparing the cable length information with a predetermined reference value to derive a difference signal therebetween, and a circuit for controlling at least one of the magnitude and phase properties of the driving signal in accordance with said difference signal.

14. An apparatus according to claim 1, wherein said cable length detection circuit comprises a modulation circuit for modulating the driving signal with a modulation signal, a demodulation circuit for demodulating a modulated component contained in the electric signal supplied from the solid state image sensor, and a phase difference detection circuit for detecting a phase difference between an output signal from the demodulation circuit and said modulation signal.

15. An apparatus according to claim 14, wherein said modulation circuit modulates the driving signal during a non-pictorial period.

16. An apparatus according to claim 15, wherein said modulation circuit phase-modulates a reset pulse contained in the driving signal.

17. An apparatus according to claim 15, wherein said modulation circuit frequency-modulates a reset pulse contained in the driving signal.

18. An apparatus according to claim 15, wherein said modulation circuit amplitude-modulates a reset pulse contained in the driving signal.

19. A video endoscope apparatus comprising an insertion section insertable into an object under inspection;
    a solid state image sensor arranged at a distal end of the insertion section for converting an optical image of the object into an electric signal;
    a video processor unit including a driving circuit for generating a driving signal for the solid state image sensor, and a video processing circuit for processing the electric signal supplied from the solid state image sensor to derive an image signal;
    a signal cable arranged within the insertion section and including a first signal line for transmitting the driving signal generated from the driving circuit to the solid state image sensor and a second signal line for transmitting the electric signal supplied from the solid state image sensor to the video processing circuit;
    a cord accommodating said signal cable and having one end connected to a proximal end of the insertion section and the other end connectable to the video processor unit via a connector;

a display device for displaying the image signal processed by the video processing circuit; and a cable length detection circuit arranged in said video processor unit for processing the electric signal supplied from the solid state image sensor through the second signal line to detect from the electric signal cable length information representing the length of said signal cable.

20. An apparatus according to claim 19, wherein said video processor unit further comprises a control circuit for controlling the driving signal supplied from the driving circuit in accordance with the cable length information representing the length of the signal cable.

21. An apparatus according to claim 20, wherein said cable length detection circuit detects a magnitude property of the electric signal supplied from the solid state image sensor via the second signal line.

22. An apparatus according to claim 21, wherein said cable length detection circuit detects an amplitude of a reset pulse portion contained in said electric signal supplied from the solid state image sensor.

23. An apparatus according to claim 21, wherein said cable length detection circuit detects a D.C. level of the electric signal supplied from the solid stage image sensor.

24. An apparatus according to claim 21, wherein said cable length detection circuit detects the magnitude property of the electric signal supplied from the solid state image sensor during a non-pictorial period.

25. An apparatus according to claim 20, wherein said cable length detection circuit detects a phase property of the electric signal supplied from the solid state image sensor via the second signal line.

26. An apparatus according to claim 25, wherein said cable length detection circuit detects a phase difference between a reset pulse portion contained in the electric signal supplied from the solid stage image sensor via the second signal line and a reset pulse contained in the driving signal to be supplied to the solid stage image sensor via the first signal line.

27. An apparatus according to claim 20, wherein said driving circuit generates horizontal and vertical driving pulses and a reset pulse for driving the solid state image sensor, and said control circuit controls at least one of D.C. level, amplitude, phase and frequency properties of one of the horizontal and vertical driving pulses and reset pulse.

28. An apparatus according to claim 19 or 27, wherein said video processor unit further comprises a control circuit for controlling the video processing circuit in accordance with the cable length information.

29. An apparatus according to claim 28, wherein said control circuit controls a gain of the image signal in accordance with the cable length information.

30. An apparatus according to claim 28, wherein said control circuit controls timings of sampling the image signal in the video processing circuit in accordance with the cable length information.

31. An apparatus according to claim 27, wherein said control circuit comprises a comparator circuit for comparing the cable length information with a predetermined reference value to derive a difference signal therebetween, and a circuit for controlling at least one of the amplitude property and phase property of the driving signal in accordance with the difference signal.

32. An apparatus according to claim 19, wherein said cable length detection circuit comprises a modulation circuit for modulating the driving signal with a modulation signal, a demodulation circuit for demodulating a modulated component contained in the electric signal supplied from the solid state image sensor via the second signal line, and a phase difference detection circuit for detecting a phase difference between an output signal from the demodulation circuit and said modulation signal.

33. An apparatus according to claim 32, wherein said modulation circuit modulates the driving signal during a non-pictorial period.

34. An apparatus according to claim 33, wherein said modulation circuit phase-modulates a reset pulse contained in the driving signal.

35. An apparatus according to claim 33, wherein said modulation circuit frequency-modulates a reset pulse contained in the driving signal.

36. An apparatus according to claim 33, wherein said modulation circuit amplitude-modulates a reset pulse contained in the driving signal.

* * * * *